(12) United States Patent
Fox et al.

(10) Patent No.: US 11,602,625 B2
(45) Date of Patent: Mar. 14, 2023

(54) UNIT FOR A MECHANICAL CONNECTING DEVICE FOR MEDICAL PURPOSES, PARTICULARLY FOR PERITONEAL DIALYSIS

(71) Applicant: PERIPAL AG, Zurich (CH)

(72) Inventors: Stephan Fox, Zurich (CH); Mirko Meboldt, Zurich (CH); Sandra Neumann, Zurich (CH)

(73) Assignee: Peripal AG, Zurich (CH)

( * ) Notice: Subject to any disclaimer, the term of this patent is extended or adjusted under 35 U.S.C. 154(b) by 14 days.

(21) Appl. No.: 16/472,905

(22) PCT Filed: Dec. 24, 2017

(86) PCT No.: PCT/EP2017/084574
§ 371 (c)(1),
(2) Date: Jun. 24, 2019

(87) PCT Pub. No.: WO2018/115530
PCT Pub. Date: Jun. 28, 2018

(65) Prior Publication Data
US 2021/0402166 A1    Dec. 30, 2021

(30) Foreign Application Priority Data

Dec. 24, 2016  (EP) ..................................... 16206896
May 16, 2017  (EP) ..................................... 17171391

(51) Int. Cl.
*A61M 39/16*    (2006.01)
*A61M 1/28*    (2006.01)
(Continued)

(52) U.S. Cl.
CPC .......... *A61M 39/165* (2013.01); *A61M 1/285* (2013.01); *A61M 39/18* (2013.01); *A61M 39/20* (2013.01)

(58) Field of Classification Search
CPC .... A61M 39/165; A61M 39/18; A61M 39/20; A61M 1/28; A61M 1/285
See application file for complete search history.

(56) References Cited

U.S. PATENT DOCUMENTS 5,611,506 A * 3/1997 Berger .................. A61M 39/18
248/65
2013/0197485 A1 * 8/2013 Gardner .............. A61M 39/162
604/533
(Continued)

FOREIGN PATENT DOCUMENTS

CA    2574551    7/2008
CN    105102055   11/2015
(Continued)

*Primary Examiner* — Nathan R Price
*Assistant Examiner* — Anh Bui
(74) *Attorney, Agent, or Firm* — JMB Davis Ben-David

(57) ABSTRACT

The invention relates to a unit (1) for an apparatus (2) for connecting and disconnecting a tubular fitting (24) to a connector (14), comprising a body (16) having: —a first receptacle (18) and a second receptacle (20), wherein each of said receptacles is configured for holding an end cap (22) of the tubular fitting (24), and —a connector holder (26) configured for accommodating insertion of the connector (14); wherein the unit (1) comprises a capsule (290) that is configured to be connected to said body (16) in a releasable fashion, wherein said capsule (290) comprises said second receptacle (20).

17 Claims, 13 Drawing Sheets

Figure 1:
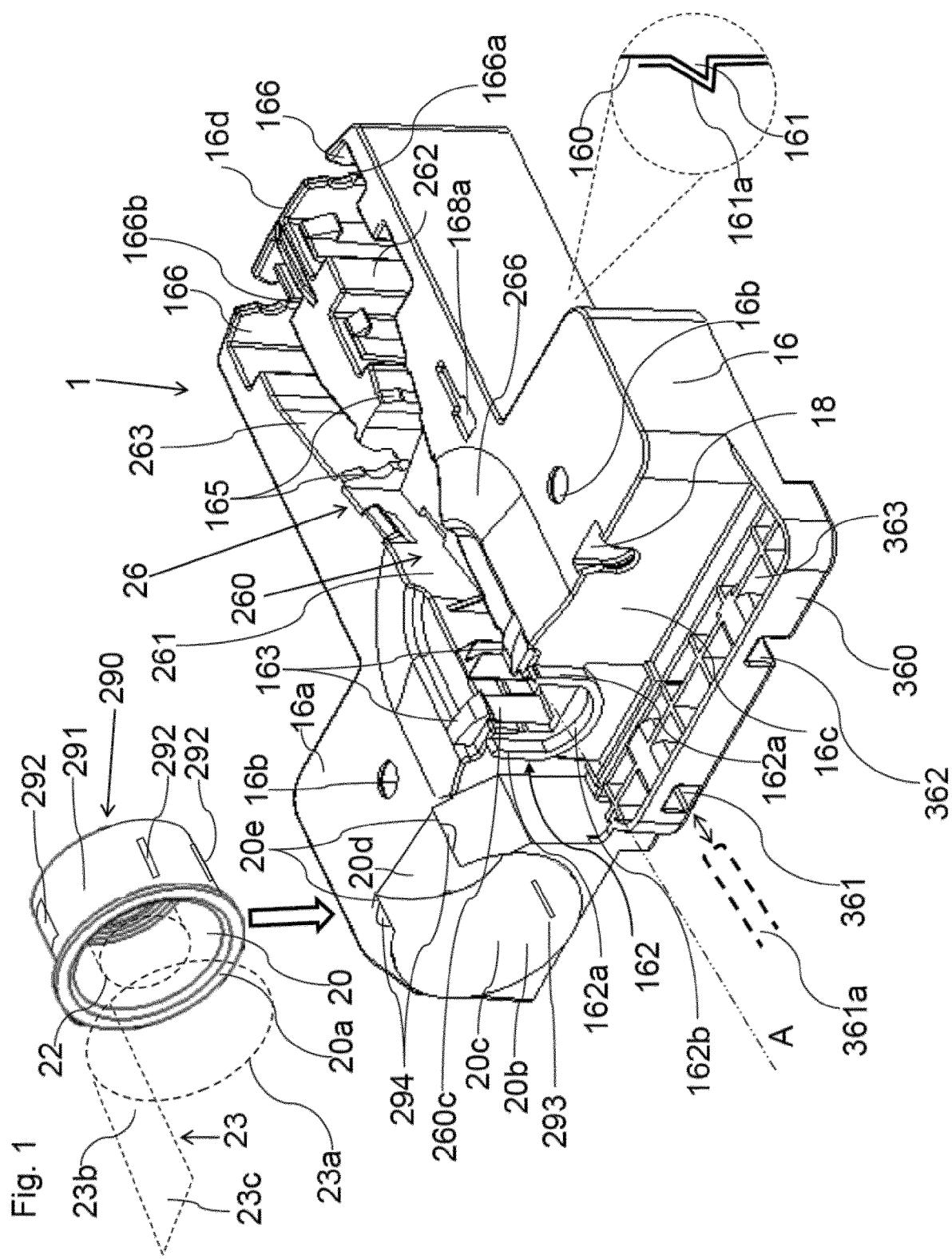

(51) Int. Cl.
*A61M 39/18* (2006.01)
*A61M 39/20* (2006.01)

(56) References Cited

U.S. PATENT DOCUMENTS

2016/0053927 A1* 2/2016 Whitaker .............. A61M 39/18
 137/15.09
2018/0161567 A1* 6/2018 Fox .................... A61M 39/162

FOREIGN PATENT DOCUMENTS

WO 2014/159346 10/2014
WO 2016/198129 12/2016

* cited by examiner

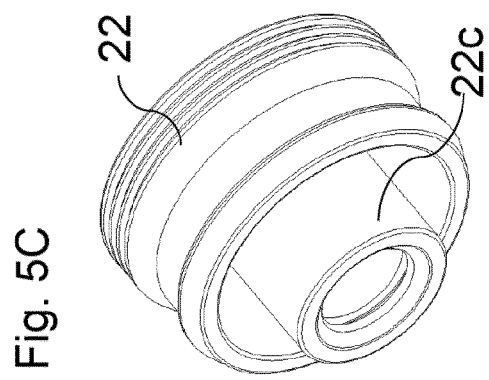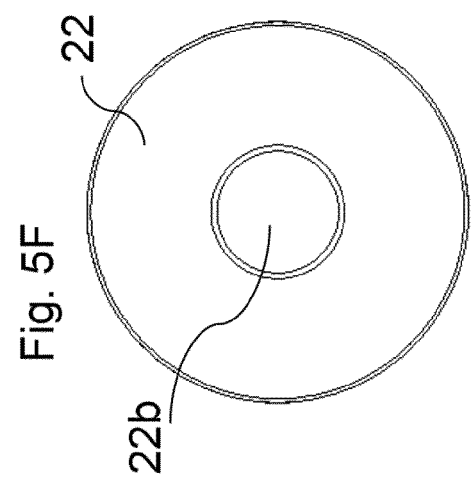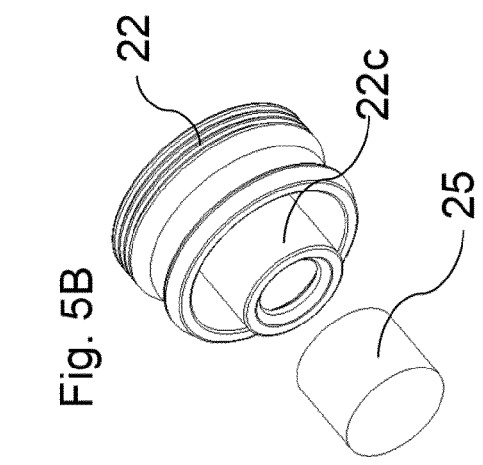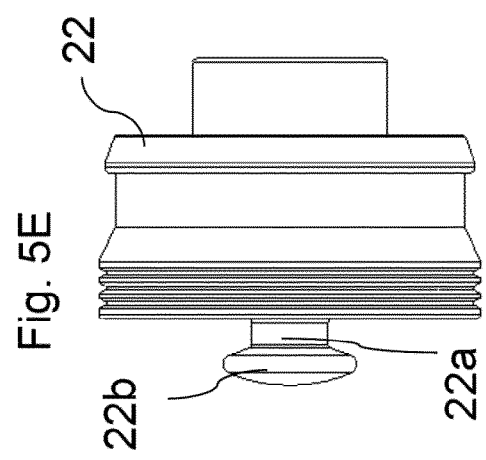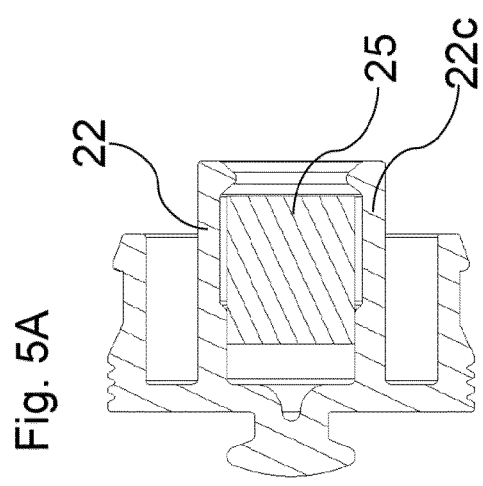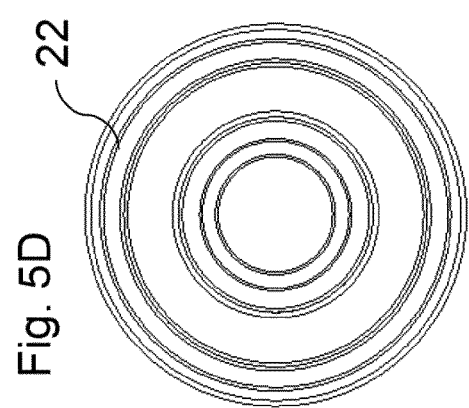

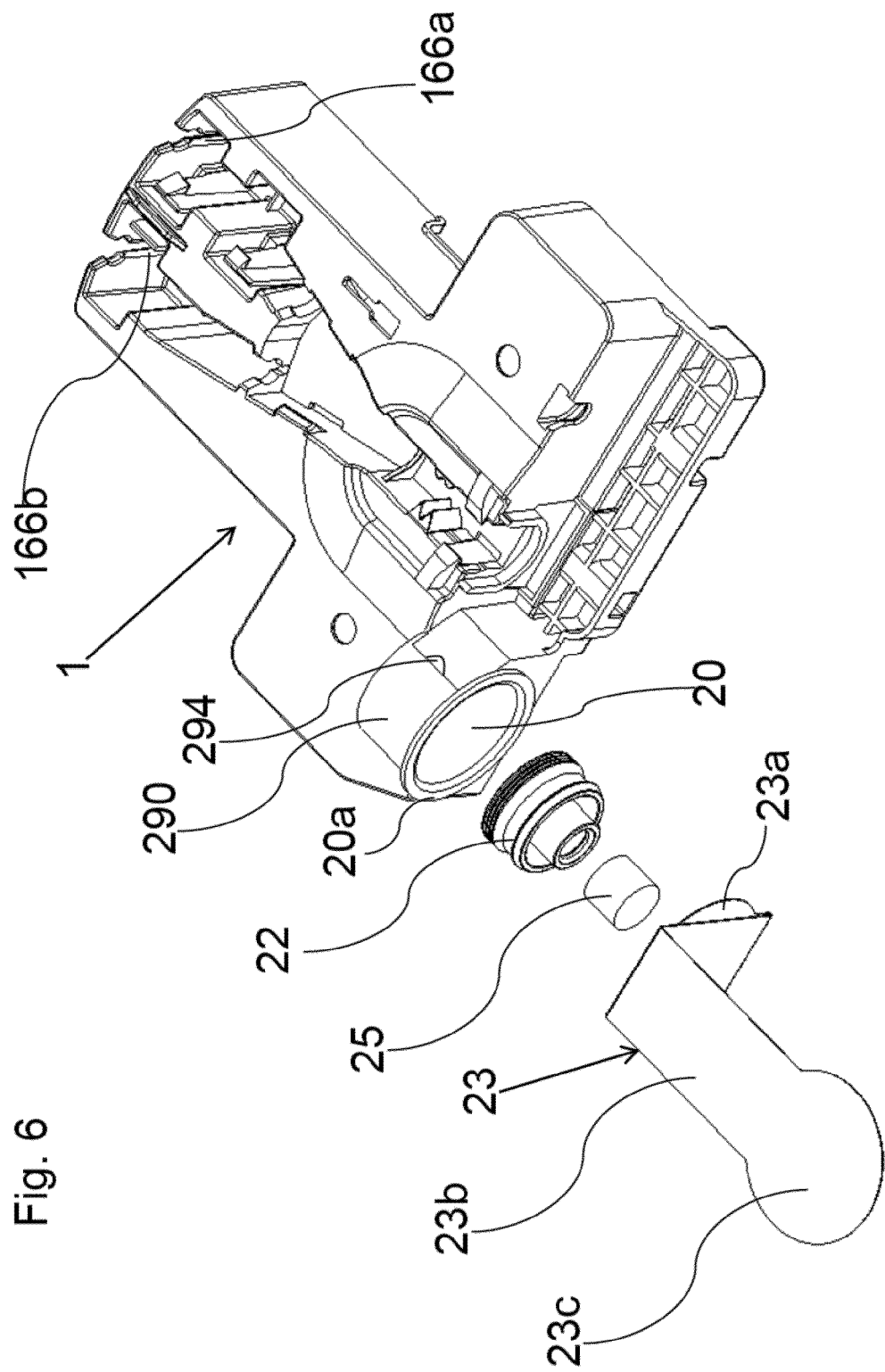

UNIT FOR A MECHANICAL CONNECTING DEVICE FOR MEDICAL PURPOSES, PARTICULARLY FOR PERITONEAL DIALYSIS

CROSS-REFERENCE TO RELATED APPLICATIONS

This is the U.S. National Stage of International Patent Application No. PCT/EP2017/084574 filed on Dec. 24, 2017, which in turn claims the benefit of European Patent Application Nos. 16206896.9 filed on Dec. 24, 2016 and 17171391.0 filed on May 16, 2017.

The present disclosure generally relates to a disposable (e.g. single use) capsule of a unit for an apparatus for connecting and disconnecting a tubular fitting to a connector for medical purposes, particularly for peritoneal dialysis, and more specifically to a removable unit for an apparatus for replacing a catheter cap in a protective and sterile environment.

Connections of tubular fittings for active fluidic delivery are often achieved by luer-lock connecting systems. Often, these conventional luer-lock connecting systems are used to perform peritoneal dialysis and the like by employing an actuating station having a pumping mechanism and associated flexible tubes or using manual therapy approaches.

A user connects and disconnects a catheter (or similar tubing, i.e. transfer set) from the user to the connecting system at least once a day, or up to five times a day for exchanging medical fluid to and from the user's peritoneal cavity. To initiate the peritoneal dialysis, an old, existing cap of the catheter is initially disconnected from the catheter, and a connection is made between the catheter and a dialysate fluid bag, or a tubing leading to a fluid or a drug delivery system (e.g. pump). For example, in the state of the art, a stability barrier of the fluid bag is removed, and the catheter is rotationally fastened to an end tube of the fluid bag. After completion of the dialysis, the user rotationally unfastens the catheter from the fluid bag and reseals the catheter with a new, sterile cap.

However, during exchanges of the catheter caps from an old one to a new one, the catheter and the fluid bag connection are typically exposed to an unsterile environment. At times, peritonitis can occur due to contamination caused by contact with the surrounding atmosphere, and accidental touching of the catheter.

Other catheter related infections can also occur due to touch or air (e.g. breath) contact during the connection and disconnection of the connecting system. This situation is undesirable to the user because bacteria and other micro-organisms can be introduced into the user's peritoneal cavity, thereby causing peritonitis or other illness. Moreover, the conventional system relies in part on the vision and/or skills of the user for properly connecting and disconnecting the catheter.

Thus, the problem underlying the present invention is to provide a device that allows replacement or interchange of end caps in a simple and sanitary manner.

This problem is solved by a unit having the features of claim 1. Preferred embodiments of the unit according to the invention are stated in the corresponding sub claims and are described below. Further aspects of the invention relating to a tubular fitting, a removable clamp and an end cap are also disclosed and claimed. Particularly, one, several or all said components (i.e. tubular fitting, removable clamp and end cap) can also be components of said unit according to the invention.

According to claim 1 a unit according to the invention for an apparatus for connecting and disconnecting a tubular fitting to a connector is disclosed, which unit comprises:

a body having: a first receptacle and a second receptacle, said first and second receptacles being particularly disposed at opposite ends of said body, wherein each of said receptacles is configured for receiving or holding an end cap of the tubular fitting, particularly to fasten or unfasten the end cap for replacement and a connector holder being particularly disposed between said first and second receptacles, and configured for accommodating insertion of the connector; and wherein preferably said body is configured to be connected to said apparatus in a releasable fashion, particularly such that the unit can be manually connected to said apparatus and manually removed from the apparatus, e.g. after its use (see below), and wherein the unit comprises a capsule that is configured to be connected to said body in an (e.g. manually) releasable fashion, wherein said capsule comprises said second receptacle.

Particularly, the position of the first and second receptacle may also be interchanged, i.e., when looking from above, the first receptacle may be arranged on the left side of the connector holder or on the right side of the connector holder. The movements of the cradle assembly/unit can be easily adapted to such a change of positions.

According to an embodiment, the capsule is configured to be sterilized for allowing multiple uses. Alternatively, the capsule is a disposable capsule that is designed for a single use within the unit, particularly comprising unfastening an end cap from the tubular fitting, connecting the connector inserted into the connector holder to the tubular fitting, disconnecting the connector from the tubular fitting, and fastening an end cap received in the second receptacle of the capsule to the tubular fitting.

Further, according to an embodiment of present invention, the body comprises a recess for receiving the capsule in a form fitting manner.

Further, according to an embodiment of present invention, the capsule and/or the body are configured to fasten the capsule to the body by a latching connection when the capsule is arranged in said recess adapted for receiving the capsule.

Further, according to an embodiment of present invention, the recess for receiving the capsule comprises a lateral wall for enclosing the capsule at least partially when the capsule is arranged in said recess.

Further, according to an embodiment of present invention, the lateral wall comprises a discontinuity arranged between two opposing edges of the lateral wall.

Further, according to an embodiment of present invention, a recess is formed in each edge, which recesses face each other. Particularly, these recesses allow for a more easy removal of the capsule from the recess for receiving the capsule.

Further, according to another embodiment of present invention, an actuating member is arranged at each edge for unlocking the latching connection between the capsule and the recess or lateral wall of the recess. The actuating members may interact with one or several members of the latching connection between the capsule and the body in order to release the latching connection.

Further, according to an embodiment of present invention, the capsule comprises a lateral wall surrounding said second receptacle. Particularly, the capsule further comprises a bottom connected (e.g. integrally) to the lateral wall of the capsule.

Further, according to an embodiment of present invention, the lateral wall of the capsule comprises at least one latching nose that is configured to engage with an associated latching recess formed in said lateral wall of said recess for receiving the capsule, or wherein the lateral wall of said recess for receiving the capsule comprises at least one latching nose that is configured to engage with an associated latching recess formed in said lateral wall of the capsule.

Further, according to an embodiment of present invention, the capsule comprises an indicator that is configured to indicate whether the capsule is unused (e.g. comprises a fresh end cap). Particularly, said indicator is arranged on the lateral wall of the capsule and can be a window or an indicator that undergoes a visually perceivable change when the capsule has been used (i.e. opened for using the end cap stored in the capsule).

Further, according to an embodiment of present invention, the unit is a removable unit, wherein said body is configured to be connected to said apparatus in a releasable fashion (see also above).

Preferably, according to an embodiment, said body comprises a latching means or latching part for connecting the body in a releasable fashion to said apparatus.

Preferably, according to an embodiment, the unit is designed to be sterilized or the like for allowing multiple uses of the unit.

Preferably, according to an alternative embodiment, the unit is a disposable unit and designed for a single use (and to be discarded thereafter) comprising at least: unfastening an end cap from the tubular fitting, connecting the connector inserted into the connector holder to the tubular fitting, disconnecting the connector from the tubular fitting, and fastening an end cap received in the second receptacle of the capsule to the tubular fitting. Thus, the capsule and the whole unit can be disposable items.

Particularly, while the capsule is preferably adapted for a single use only, the unit may be designed for a finite number of such uses. Here, particularly, the removable unit is to be discarded before the end of the lifetime of the apparatus and to be substituted by a new removable unit.

Further, particularly, the connector (e.g. a so called Y-set forming part of the dialysis system) comprises a first conduit, which first conduit comprises a frangible inline seal, and a second conduit, wherein the two conduits branch off from an end section of the connector, which end section is configured to be connected to the tubular fitting (which e.g. forms part of or is connected to a catheter/transfer set) or disconnected from the tubular fitting, and wherein the tubular fitting comprises a member which is configured to be actuated so as to open or close the tubular fitting (or catheter) for allowing or preventing the passage of fluid through the tubular fitting.

In this regard, a single use of the disposable device particularly comprises the following steps (e.g. in case of CAPD):

providing the tubular fitting with an end cap fastened to the tubular fitting, wherein the end cap is received/held in the first receptacle of the body of the disposable device/cradle assembly, wherein the cradle assembly resides in a first position and is formed by the unit and a moveable carrier of the apparatus, which unit is connected to said carrier, and wherein the tubular fitting is inserted into the holder assembly, particularly removing a peal-off seal of the capsule (that is e.g. inserted into the recess of the body of the unit) to open the second receptacle of the capsule which contains an end cap, moving the cradle assembly (see below)/unit away from the holder assembly so as to unfasten the end cap from the tubular fitting, moving the cradle assembly into the second position and then towards the holder assembly so as to connect the connector inserted into the connector holder to the tubular fitting, preferably opening the tubular fitting (e.g. by allowing the patient or user to actuate said member on the tubular fitting) so as to drain a liquid or fluid, and closing the tubular fitting thereafter using said member, breaking the frangible inline seal using a first actuating member of the apparatus (see below), flushing both conduits by letting fluid flow through the first and the second conduit while the tubular fitting is closed for preventing the passage of fluid through the tubular fitting, preferably opening the tubular fitting using said member, e.g. by allowing the patient or user to actuate said member on the tubular fitting to let liquid or fluid flow (e.g. towards the target) before closing the tubular fitting using said member again, interrupting the second conduit by actuating a third actuating member of the apparatus and opening the tubular fitting by actuating said member of the tubular fitting, preferably letting fluid pass through the first conduit, the end section, and the tubular fitting towards a target, closing the tubular fitting by actuating said member of the tubular fitting, interrupting the first conduit for preventing the passage of fluid through the first conduit by actuating the second actuating member, closing the tubular fitting (by using said member) for preventing the passage of fluid through the tubular fitting, preferably preventing any disconnection of the liquid of fluid line or between the tubular fitting and the connector before the tubular fitting is not closed (e.g. by an preferably mechanical detecting means that is configured to detect the opening/closing status) and preventing retraction (e.g. of the tubular fitting) into the housing in case the tubular fitting is open. (Said detecting means may also be a mechanical means that is configured to prevent said retraction when the tubular fitting is open and allows the passage of fluid through the tubular fitting).

moving the cradle assembly away from the holder assembly so as to disconnect the connector from the tubular fitting, and moving the cradle assembly into the third position and towards the holder assembly so as to fasten said end cap received in the second receptacle of the disposable capsule to the tubular fitting.

Particularly, the above described use corresponds to a CAPD, wherein particularly, in case of an APD said steps are also conducted with the difference that the first, the second and the third actuating members are not used and particularly only a single conduit of the connector is present that leads to a cycler (which single conduit is arranged in the second region of the recess, while the first region stays empty):

providing the tubular fitting with an end cap fastened to the tubular fitting, wherein the end cap is received/held in the first receptacle of the body of the unit/cradle assembly, wherein the cradle assembly resides in a first position and is formed by said (e.g. removable) unit and said moveable carrier of the apparatus, which unit is connected to said carrier, and wherein the tubular fitting is inserted into the holder assembly, moving the cradle assembly/unit away from the holder assembly so as to unfasten the end cap from the tubular fitting, moving the cradle assembly into the second position and then towards the holder assembly so as to connect the connector (comprising a single conduit) inserted into the connector holder to the tubular fitting, preferably adding a removable clamp from above to arrest the connection between the tubular fitting and the connector while the tubular fitting is arranged in the holder assembly and the connector is arranged in the connector holder (e.g. recess of removable unit), removing the tubular fitting and the connector connected thereto from the apparatus (and particularly from the removable unit), opening the tubular fitting by actuating said member of the tubular fitting for letting fluid pass through the tubular fitting/connector, closing the tubular fitting by actuating said member of the tubular fitting, reinserting the tubular fitting and the connector into the apparatus/removable unit, preferably removing said removable clamp, particularly removing a peal-off seal of the capsule to open the second receptacle of the capsule which contains an end cap, and moving the cradle assembly away from the holder assembly so as to disconnect the connector from the tubular fitting and so as to move said member of the tubular fitting back into the housing, moving the cradle assembly into the third position and towards the holder assembly so as to fasten said end cap received in the second receptacle of the capsule to the tubular fitting.

After these complete cycles (e.g. APD or CAPD), the capsule (and particularly unit) can be discarded (e.g. together with the inserted connector and tubings connected thereto) and a new capsule is inserted into the unit of the apparatus for the next use cycle.

According to a preferred embodiment of the unit according to the present invention, the (e.g. removable) unit comprises an end cap arranged in the second receptacle formed by the capsule, wherein said end cap is completely arranged in said second receptacle. Said end cap can comprise a material and/or a Shore hardness as specified below.

Further, according to a preferred embodiment of the unit according to the present invention, said second receptacle is closed, particularly hermetically closed, by a closure comprising a peel-off seal (particularly a peal-off foil), which peel-off seal is attached to the capsule, particularly to a circumferential face side of the capsule, e.g. of the lateral wall of the capsule (the face side can face away from the bottom of the capsule, which bottom is connected to the lateral wall of the capsule).

Further, according to a preferred embodiment of the removable unit according to the present invention, said closure comprises a flexible strip connected to the peel-off seal, which strip comprises a free end section which can optionally be configured to be arranged between a bottom and a cover of a housing of said apparatus such that the free end section of the strip protrudes out of the housing and thus forms a handle by means of which the peel-off seal can be peeled off the capsule/second receptacle from outside said housing (particularly said free end section protrudes out of the housing when the cradle assembly of the apparatus resides in the third position and has been moved towards the holder assembly). This is particularly useful for CAPD. However said end section (e.g. in case of APD) or handle can also be arranged in the housing and may be accessed after the housing has been opened.

Further, according to a preferred embodiment of the unit according to the present invention, a flexible carrier member, particularly a sponge, that carries (e.g. has absorbed) an anti-bacterial fluid, is in contact with said end cap and is arranged in the receptacle that is in turn closed by said peel-off seal.

Further, according to an embodiment, said end cap comprises a disinfectant (e.g. a compound, substance or material that is characterized by an antimicrobial property, i.e., inhibits and/or destroys microorganisms), wherein particularly said end cap is at least partially or completely formed out of said disinfectant, or comprises a coating comprising said disinfectant.

Further, as already indicated above, according to a preferred embodiment of the unit according to the present invention, the body is configured to be connected to a movable carrier (also denoted as carriage) of said apparatus in a releasable fashion, wherein particularly said carrier is movable with respect to the bottom of the housing of the apparatus so that the unit can be moved together with said carrier inside said housing (carrier and removable unit form parts of said cradle assembly of the apparatus).

Further, according to a preferred embodiment of the unit according to the present invention, the body comprises a top side, wherein particularly said discontinuity of the lateral wall of the recess is arranged at the top side.

Further, according to a preferred embodiment of the unit according to the present invention, two through-holes are formed in the body on the top side which are each configured to receive an associated pin protruding from said carrier when the body is connected to the carrier, wherein particularly a face side of the respective pin is flush with the top side when the removable unit is connected to the carrier.

Further, according to a preferred embodiment of the unit according to the present invention, the top side comprises a through-hole which indicates the position of a frangible inline seal of a first conduit of the connector.

Further, according to a preferred embodiment of the unit according to the present invention, for establishing said releasable connection between the body and the carrier, the body comprises two opposing internal surfaces (e.g. extending perpendicular to said top side), wherein said internal surfaces face each other, and wherein a latching means, particularly a latching nose, is provided on each internal surface for engaging with a complementary latching means, particularly a recess, of the carrier.

Further, according to a preferred embodiment of the unit according to the present invention, the body of the unit comprises a front side wall and an opposing back side wall. Particularly, the recess of the body for receiving the capsule is arranged on the front side wall.

Further, according to a preferred embodiment of the unit according to the present invention, the connector holder comprises a recess for receiving the connector (e.g. of the dialysis system, e.g. a Y-set in case of CAPD or a patient line, e.g. a single conduit, in case of APD), which recess is arranged on the top side and extends from the front side wall to the back side wall of the body of the removable unit.

Further, according to a preferred embodiment of the unit according to the present invention, the recess comprises a Y-shape, namely an end region extending from the front side wall, which end region branches out into a first and a second region that extend from said end region to the back side wall, respectively, wherein said recess is configured to receive a (Y-shaped) connector comprising a first conduit and a second conduit, wherein the two conduits branch off from an end section of the connector, via which end section the connector is configured to be connected to said tubular fitting, wherein the end region of the recess is configured to receive said end section of the connector, and wherein the first region of the recess is configured to receive the first conduit, and wherein the second region of the recess is configured to receive the second conduit of the connector.

Particularly in case of APD, the connector comprises at least one conduit, particularly a single conduit, connected to the end section of the connector, wherein here said at least one conduit/single conduit is arranged in the second region of the recess while the first region stays empty.

Further, according to a preferred embodiment of the unit according to the present invention, the unit comprises a protrusion, particularly a U-shaped protrusion, protruding from the front side wall and extending along the end region of the recess on the front side wall, wherein said protrusion is configured to prevent an inclination of the end section of the connector with respect to an axial direction of the end section when said end section is inserted in said end region of the recess. Particularly, said protrusion comprises two opposing parallel sections that are integrally connected by a curved section which parallel sections and curved section are configured to butt against said end section in a form fitting manner to prevent said inclination.

Further, according to a preferred embodiment of the unit according to the present invention, the body comprises two holding means or holding parts arranged on the top side of the body, wherein the two holding means or parts are arranged on opposing sides of the end region of the recess for holding the end section of the connector in the end region of the recess when said end section is arranged in said end region of the recess.

Particularly, each of said two holding means or parts comprises a free end, wherein the respective free end protrudes past an associated side wall of the end region of the recess, which two side walls of said end region of the recess face each other.

Further, according to a preferred embodiment of the unit according to the present invention, the body comprises two holding means or two holding parts, wherein each of said holding means or parts forms a tooth structure, and wherein the respective holding means or part protrudes from an associated sidewall of the end region of the recess, wherein said two sidewalls face each other, and wherein said tooth structures are configured to prevent a movement of the end section of the connector in an axial direction when said end section of the connector is arranged in said end region of the recess and a force pulls said end section of the connector in said axial direction that particularly points away from said front side wall.

Further, according to a preferred embodiment of the unit according to the present invention, the body comprises a holding means or holding part arranged in the first region of the recess, which holding means or part is configured to clamp the first conduit of the connector when said first conduit is arranged in the first region of the recess, wherein particularly said holding means or part is configured to encompass said first conduit, and/or wherein the body comprises a holding means or a holding part arranged in the second region of the recess, which holding means or part is configured to clamp the second conduit of the connector (or said at least one conduit/single conduit) when said second conduit (or said at least one conduit/single conduit) is arranged in the second region of the recess, wherein particularly said holding means or part is configured to encompass said second conduit (or said at least one conduit/single conduit).

Further, according to a preferred embodiment of the unit according to the present invention, the body comprises a holding means or a holding part arranged in the first region of the recess at the back side wall, which holding means or part is configured to clamp the first conduit of the connector when said first conduit is arranged in the first region of the recess, wherein particularly said holding means or part is configured to encompass said first conduit, wherein said holding means or part comprises a slot into which the first conduit can be pushed so that the first conduit is blocked for the passage of fluid through the first conduit, and/or wherein the body comprises a holding means or a holding part arranged in the second region of the recess at the back side wall, which holding means or part is configured to clamp the second conduit (or said at least one conduit/single conduit) of the connector when said second conduit (or said at least one conduit/single conduit) is arranged in the second region of the recess, wherein particularly said holding means or part is configured to encompass said second conduit (or said at least one conduit/single conduit), and wherein said holding means or part comprises a slot into which the second conduit (or the at least one conduit/single conduit) can be pushed so that the second conduit (or the at least one conduit/single conduit) is blocked for the passage of fluid through the respective conduit.

According to an alternative embodiment, the body comprises a holding means arranged in the first region of the recess at the back side wall, which holding means is configured to clamp the first conduit of the connector when said first conduit is arranged in the first region of the recess, wherein said holding means comprises a clamping surface and a pivotable clamping arm, wherein the clamping arm is configured to be pivoted towards the clamping surface into a clamping position so that the first conduit is blocked when it is clamped between said clamping surface and the clamping arm.

Likewise, according to an embodiment, the body can comprise a holding means arranged in the second region of the recess at the back side wall, which holding means is configured to clamp the second conduit or said at least one conduit of the connector when said second conduit or said at least one conduit is arranged in the second region of the recess, wherein said holding means comprises a clamping surface and a pivotable clamping arm, wherein the clamping arm is configured to be pivoted towards the clamping surface into a clamping position so that the second conduit or said at least one conduit is blocked when it is clamped between said clamping surface and said clamping arm.

The clamping surfaces can be inclined with respect to the top side of the body.

Further, according to an embodiment, the clamping arm of the holding means of the first region of the recess is configured to be pivoted towards the associated clamping surface by means of an actuating member of the apparatus. Further, the clamping arm of the holding means of the second region of the recess may also be configured to be pivoted towards the associated clamping surface by means of an actuating member of the apparatus.

Further, according to an embodiment, the holding means of the first region of the recess comprises a hook for engaging with the clamping arm so as to hold the clamping arm in its clamping position. Furthermore, according to an embodiment, and/or wherein the holding means of the second region of the recess comprises a hook for engaging with the clamping arm so as to hold the clamping arm in its clamping position.

Further, according to an embodiment, the holding means of the first region of the recess comprises a guiding arm for guiding said actuating member of the apparatus, and/or wherein the holding means of the second region of the recess comprises a guiding arm for guiding said actuating member of the apparatus.

Particularly in case the holding means described above comprises said pivotable clamping arms, it is also possible that the unit according to the present invention comprises a capsule that is rigidly connected to the body of the unit and cannot be removed from the body of the unit. In this regard, according to a further aspect of the present invention, the following unit is disclosed:

A unit for an apparatus for connecting and disconnecting a tubular fitting to a connector, comprising:
a body having:
  a first receptacle and a second receptacle, wherein each of said receptacles is configured for holding an end cap of the tubular fitting, and
  a connector holder configured for accommodating insertion of the connector.

Here, particularly the second receptacle is rigidly connected to the body and cannot be removed from the body.

Further, particularly, this unit comprises an end cap arranged in said second receptacle formed by the body of the unit, wherein particularly said end cap is completely arranged in said second receptacle.

Further, particularly, said second receptacle is closed, particularly hermetically closed, by a closure comprising a peel-off seal, which peel-off seal is particularly attached to a circumferential face side of a lateral wall of the second receptacle, which lateral wall is formed by the body.

This unit may further comprise the features as described herein and may be used with all other aspects of the present invention described herein.

Further, according to a preferred embodiment of the removable unit according to the present invention, the body comprises a first and a second latching nose at the first region of the recess, wherein the respective latching nose is configured to engage an associated actuating member of the apparatus so as to hold the respective actuating member in a pressed position, wherein particularly the first latching nose is configured to engage with a first actuating member of the apparatus that is configured to break said frangible inline seal of the first conduit. Further, particularly the first latching nose is configured to engage such with the first actuating member that the latter ensures the passage of fluid through the first conduit after breaking of the inline seal.

Further, particularly, the second latching nose is configured to engage with a second actuating member of the apparatus that is configured to press the first conduit in said slot of the first region of the recess.

Furthermore, according to an embodiment, the body comprises a third latching nose at the second region of the recess, wherein said third latching nose is configured to engage an associated actuating member of the apparatus so as to hold said actuating member in a pressed position, wherein particularly the third latching nose is configured to engage with a third actuating member of the apparatus that is configured to press the second conduit in said associated slot of the second region of the recess.

Further, according to a preferred embodiment of the unit according to the present invention, the unit comprises a drip pan that protrudes from the front side wall of said body and is arranged below the end region of the recess as well as below the first receptacle to receive spilled fluid, wherein said drip pan comprises a plurality of dents for receiving spilled fluid.

Further, according to a preferred embodiment of the unit according to the present invention, the drip pan comprises a centering means in the form of a recess for receiving a guiding means of the apparatus, particularly in the form of a guiding pin. The drip pan may comprise a further recess for receiving said pin when the removable unit is arranged in the apparatus (with the removable unit being arranged in the first position).

Further, according to a preferred embodiment of the unit according to the present invention, the body of the unit comprises a Shore hardness in the range from 60 A to 100 A, particularly 70 A to 90 A, particularly 80 A.

Further, according to a preferred embodiment of the unit, the body comprises a material or is formed out of a material, which material is one of: polypropylene (PP); acrylonitrile butadiene styrene (ABS); a mixture of polycarbonate (PC) and acrylonitrile butadiene styrene (ABS).

According to yet another aspect of the present invention, a tubular fitting for use with the unit/apparatus is disclosed, wherein the tubular fitting is configured to be received by an opening of a body of a holder assembly of said apparatus. Particularly, according to yet another aspect of the present invention, a catheter system is disclosed which comprises a catheter and a tubular fitting and/or a connector as described herein, wherein particularly the first portion of the tubular fitting described below is configured to be in fluid communication with a lumen of the catheter (or can be brought in fluid communication with said lumen of the catheter, particularly by means of said member described herein).

Further, according to an embodiment of the tubular fitting according to the invention, the tubular fitting is configured such that an end cap can be fastened to the tubular fitting by plugging the end cap into said opening, and wherein the tubular fitting is configured such that an end cap can be unfastened from tubular fitting by pulling the end cap out of said opening.

Further, according to an embodiment of the tubular fitting according to the invention, tubular fitting is configured such that a connector can be connected to the tubular fitting by plugging the connector into said opening of the tubular fitting, and wherein the tubular fitting is configured such that a connector can be disconnected from the tubular fitting by pulling the connector out of said opening of the tubular fitting.

Further, preferably, said plugging and/or pulling is irrotational.

Further, according to an embodiment of the tubular fitting according to the invention, the tubular fitting is formed as an adapter, which comprises a first recess at a first end of the adapter, which first recess comprises an internal thread configured to be rotationally fastened to an external thread of a first portion of a catheter, and wherein the adapter comprises a shroud at an opposite second end of the adapter, which shroud surrounds a second recess of the adapter into which a protrusion of the adapter protrudes, which protrusion comprises said opening of the adapter such that the shroud surrounds said protrusion and said opening of the adapter, wherein the shroud is coaxially arranged with respect to said protrusion.

To describe the adapter function in more detail, the tubular fitting will be described below in terms of a first and a second portion of the tubular fitting.

According thereto, in a preferred embodiment of the tubular fitting according to the present invention, the tubular fitting comprises a first portion. Particularly, the first portion is configured to be connected to a catheter or may form part of such a catheter, e.g. of a transfer-set (e.g. a mini-set). Furthermore, the tubular fitting comprises an adjacent second portion comprising said opening of the tubular fitting for connecting with an connector or for fastening an end cap to the second portion/tubular fitting.

Further, according to a preferred embodiment of the tubular fitting according to the present invention, the second portion is configured such that an end cap can be fastened to the second portion by plugging the end cap into said opening of said second portion (e.g. upon said movement of the cradle assembly or removable unit towards the holder assembly when the cradle assembly/removable unit is in the third position), and wherein the second portion is configured such that an end cap can be unfastened from the second portion by pulling the end cap out of said opening, (e.g. upon said movement of the cradle assembly or removable unit away from the holder assembly when the cradle assembly/removable unit is in the first position).

Further, according to a preferred embodiment of the tubular fitting according to the present invention, the second portion is configured such that a connector can be connected to the second portion by plugging the connector into said opening of said second portion (e.g. upon said movement of the cradle assembly or removable unit towards the holder assembly when the cradle assembly/removable unit is in the second position), and wherein the second portion is configured such that a connector can be disconnected from the second portion by pulling the connector out of said opening (e.g. upon said movement of the cradle assembly or removable unit away from the holder assembly when the cradle assembly/removable unit is in the second position).

Further, particularly, as already indicated, said plugging and/or pulling is preferably irrotational (i.e. does not involve any rotation of the second portion/tubular fitting or of the respective end cap).

Further, according to a preferred embodiment of the tubular fitting according to the present invention, the tubular fitting comprises a removable clamp for arresting the connector with respect to the tubular fitting (e.g. with respect to the second portion) when the connector is connected to the tubular fitting (e.g. to the second portion), wherein particularly the clamp is configured to be connected to the tubular fitting (e.g. to the second portion), particularly by means of a clip-on connection, wherein particularly the clamp encompasses the tubular fitting (e.g. the second portion) when it is connected to the tubular fitting (e.g. to the second portion).

Further, according to an embodiment of the tubular fitting according to the present invention, the second portion is formed as an adapter (see also above), which comprises a first recess at a first end of the adapter, which first recess comprises an internal thread configured to be rotationally fastened to an external thread of the first portion, particularly such that a lumen surrounded by the first portion is in flow communication with a lumen surrounded by the adapter. Preferably, the first recess comprises a conical shape. Further, preferably, the external thread is formed on a conical section of the first portion. Furthermore, preferably, the adapter comprises a shroud, preferably a bell-shaped shroud, at an opposite second end of the adapter, which shroud surrounds a second recess of the adapter into which second recess a protrusion of the adapter protrudes, which protrusion preferably comprises said opening of the adapter such that the shroud surrounds said protrusion and said opening of the adapter. Further, the shroud is preferably coaxially arranged with respect to said protrusion.

Further, according to an alternative embodiment, the second portion may be integrally connected to the first portion (which in turn may be connected to said catheter), particularly such that the two portions (i.e. their lumina) are in flow communication with each other.

Here, particularly, the second portion comprises a shroud, which shroud surrounds a recess of the second portion into which a protrusion of the second portion protrudes, which protrusion comprises said opening of the second portion such that the shroud surrounds said protrusion and said opening of the second portion, wherein the shroud is coaxially arranged with respect to said protrusion.

Further, according to a preferred embodiment of the tubular fitting according to the present invention, the clamp is configured to cover a portion of the shroud and of the second recess when the clamp is connected to the tubular fitting (e.g. to the second portion), wherein the clamp is configured to engage behind a portion of the connector when the connector is connected to the tubular fitting (e.g. to the second portion) so that the connector cannot be disconnected from the tubular fitting (e.g. from the second portion).

Further, according to a preferred embodiment of the present invention, the clamp is configured to be connected to the tubular fitting (e.g. to the second portion) and/or removed from the tubular fitting (e.g. from the second portion) when the tubular fitting is arranged in a holder assembly of an apparatus to which said removable unit is connected.

Further, according to a preferred embodiment of the tubular fitting according to the present invention, the clamp comprises two arms extending from a base of the clamp for encompassing the tubular fitting, particularly its second portion.

Further, according to a preferred embodiment of the tubular fitting according to the present invention, the clamp comprises an inner protrusion (e.g. at a position where the shroud ends) for insertion into a circumferential groove of the tubular fitting, particularly of the second portion, when the clamp is connected to the tubular fitting, e.g. to the second portion.

Further, according to a preferred embodiment of the tubular fitting according to the present invention, the clamp comprises a flap for removing the clamp from the tubular fitting, which flap is connected to the base, particularly via a hinge, wherein particularly, for forming said hinge, the clamp comprises a through-hole arranged between the base and the flap.

Further, according to yet another aspect of the present invention, a removable clamp is disclosed, for arresting a connector with respect to a tubular fitting when the connector is connected to the tubular fitting. Such a removable clamp is particularly useful for an APD when the tubular fitting and the connector are connected and removed from the apparatus. This ensures that the connection between these two components can be maintained.

Particularly, the removable clamp is configured to be connected to the tubular fitting, particularly by means of a clip-on connection, wherein particularly the clamp encompasses the tubular fitting when it is connected to the tubular fitting.

Further, according to an embodiment of the removable clamp according to the invention, the clamp is configured to cover a portion of a shroud and of an opening of the tubular fitting when the clamp is connected to the tubular fitting, wherein the clamp is configured to engage behind a portion of the connector when the connector is connected to the tubular fitting so that the connector cannot be disconnected from the tubular fitting.

Further, according to an embodiment of the removable clamp according to the invention, the clamp is configured to be connected to the tubular fitting and/or removed from the tubular fitting when the tubular fitting is arranged in a holder assembly of an apparatus.

Further, according to an embodiment of the removable clamp according to the invention, the removable clamp comprises two arms extending from a base of the clamp for encompassing the tubular fitting (e.g. the second portion of the tubular fitting).

Further, according to an embodiment of the removable clamp according to the invention, the clamp comprises a protrusion for insertion into a circumferential groove of the tubular fitting when the clamp is connected to the tubular fitting.

Further, according to an embodiment of the removable clamp according to the invention, the clamp comprises a flap for removing the removable clamp from the tubular fitting, which flap is connected to the base, particularly via a hinge, wherein particularly, for forming said hinge, the clamp comprises a through-hole arranged between the base and the flap.

Further, according to yet another aspect of the present invention, an end cap for use with a tubular fitting and a unit is disclosed, which end cap is configured to be connected to the tubular fitting so as to close the tubular fitting.

Further, according to an embodiment of the end cap according to the invention, the end cap comprises a protrusion having a broadened head (i.e. the head comprises a diameter that is larger than a diameter of a section of said protrusion that connects the head to a back side of the end cap). Particularly, said head is configured to engage behind an edge of a first receptacle of the unit, so that the tubular fitting can be pulled off the end cap when the latter has its head engaged with said edge of the first receptacle.

Further, according to an embodiment of the end cap according to the invention, the end cap comprises a flexible means, particularly a sponge, that carries an anti-bacterial agent or fluid.

Further, according to an embodiment of the end cap according to the invention, the end cap comprises a disinfectant (e.g. a compound, substance or material that is characterized by an antimicrobial property, i.e., inhibits and/or destroys microorganisms), wherein particularly said end cap is at least partially or completely formed out of said disinfectant, or comprises a coating comprising said disinfectant.

Further, according to yet another aspect of the present invention, an apparatus for connecting and disconnecting a tubular fitting to a connector is disclosed. According to this aspect of the present invention, the apparatus comprises an (e.g. removable) unit according to the present invention, particularly according to one of the various embodiments described and claimed herein.

Particularly, said apparatus according to the invention comprises:
a cradle assembly configured for accommodating the connector, the cradle assembly including the unit, which unit comprises a body having:
a first receptacle and a second receptacle, said first and second receptacles being particularly disposed at opposite ends of said body, wherein particularly each of said receptacles is configured for receiving or holding an end cap of the tubular fitting, particularly to fasten or unfasten the end cap for replacement, and wherein the unit comprises a capsule that is configured to be connected to said body in a releasable fashion, wherein said capsule comprises said second receptacle;
a connector holder being particularly disposed between said first and said second receptacle, and configured for accommodating insertion of the connector;
a holder assembly configured for accommodating insertion of the tubular fitting; and particularly
a means or member configured for operating said cradle assembly so that said cradle assembly is reciprocable (i.e. movable back and forth) in a transverse direction relative to said holder assembly between a first position, a second position, and a third position.

Particularly, the (e.g. removable) unit according to the invention is adapted for the use with such an apparatus for connecting and disconnecting a tubular fitting to a connector, which apparatus particularly uses an enclosed, movable cradle assembly configured for accommodating said connector, particularly a fluid bag connector (herein the invention is often described in terms of a fluid bag connector, but may also be used with any other connector). Furthermore, particularly, the notion catheter refers to medical catheters, but particularly also to all other structures or conduits via which a fluid can be delivered and which structures or conduits can be closed with a cap. Further, particularly, the notion cap or end cap refers to all kinds of closures that can be used in a reasonable manner in the framework of the present invention.

Particularly, said apparatus according to the present invention is designed to mechanically connect a Peritoneal Dialysis (PD) catheter to a dialysis bag during continuous ambulatory peritoneal dialysis (CAPD) procedure and also with APD, automated peritoneal dialysis when connected to a PD cycler. The apparatus is particularly intended for use by home dialysis patients, caregivers and health care professionals at home or within health care facilities.

Further, particularly, the adapter/tubular fitting according to the invention is designed to transform a rotational Luer movement into a linear movement so that connecting/disconnecting or fastening/unfastening can be performed in a rotation free manner by means of merely linear plugging or pulling movement.

Particularly, the adapter/tubular fitting according to the invention is intended to mate two devices together and is—according to an embodiment—either protected by the closure cap (also denoted end cap) or connected to the dialysis bag (or any tubing connected to a drug or a drug delivery system) during the therapy. Particularly, the adapter is fastened to the catheter (or e.g. a transfer set, for instance mini-set) of the patient and particularly rests there for the e.g. 6 months said catheter (or e.g. a transfer- or mini-set) is in use.

Further, particularly, the end cap of the unit is intended to be used for closure of the adapter when no dialysis bag is attached to perform the therapy. Particularly, it is held in place with a secured sealed locking mechanism.

Further, particularly, the apparatus comprises a housing for receiving the body of the unit that is configured to hold the connector and end caps to be fastened to or unfastened from the tubular fitting. Thus, this body ensures an antibacterial conduction of the connecting/disconnecting or fastening/unfastening (end caps) operations. It is preferably pre-filled/pre-assembled with the new (sterile) end cap that resides in the disposable capsule. Prior to the connecting operation, said body may be pre-filled with a sterile end cap, e.g. by inserting a capsule holding the end cap into the recess of the body of the unit, and is then assembled onto a moveable carrier of the cradle assembly. These components assist in connecting an e.g. PD catheter to an e.g. dialysis bag during a CAPD or APD procedure.

Particularly, the apparatus comprising the above described components is intended to be used as a patient aid in home dialysis therapy. Particularly, it supports the connection of the e.g. catheter to the e.g. dialysis bag. It performs this connection mechanically in an easy manner, therefore providing a convenient alternative to the conventional connection performed completely manually.

Particularly, said holder assembly includes a body having an opening for receiving the tubular fitting.

Further, particularly, the cradle assembly (i.e. the unit and the moveable carrier) is configured to be movable in each of said positions towards and away from the holder assembly by means of said means for operating the cradle and holder assembly, preferably in a direction perpendicular to said transverse direction.

Further, particularly, when the cradle assembly is in the first position, the cradle assembly is movable away from the holder assembly so as to unfasten an end cap received/held in the first receptacle, which end cap is fastened to a tubular fitting, from the tubular fitting that is inserted into the holder assembly.

Further, particularly, when the cradle assembly is in the second position, the cradle assembly is movable towards the holder assembly so as to connect a connector inserted into the connector holder to a tubular fitting inserted into the holder assembly so that a flow connection is established between said connector and the tubular fitting, or wherein the cradle assembly is moveable away from the holder assembly so as to disconnect a connector inserted into the connector holder and connected to a tubular fitting that is inserted into the holder assembly from the tubular fitting.

Further, particularly, the apparatus comprises a housing.

Further, according to an embodiment of the apparatus according to the invention, said body of the unit can be (e.g. manually) released from a movable carrier of the cradle assembly that is moveable in said positions. Further, particularly, the connected catheter-dialysis fluid line (comprising in an embodiment at least the tubular fitting and the connector as well as particularly conduits connected thereto) can be removed from the housing when the cradle assembly is in the second position and has particularly been moved towards the holder assembly, e.g. in order to allow application of the device for APD.

Furthermore, preferably, the housing comprises a cover that can be opened and/or removed from the housing (e.g. from a bottom of the housing) and is preferably at least partially or completely transparent, particularly so as to be able to observe said fastening/unfastening of the end caps and said connecting of the tubular fitting to the connector or said disconnecting of the tubular fitting from the connector.

Further, according to an embodiment, the holder assembly is fixed to the housing, particularly bottom of the apparatus and cannot move with respect to the housing. When the tubular fitting is received in the holder assembly as intended, said member for opening/closing the tubular member protrudes out of the housing and is accessible for the user so that the user can open/close the tubular fitting for the passage of fluid by means said member.

Further, particularly, the holder assembly and/or the tubular fitting may be configured to move together with the cradle assembly/unit when the cradle assembly/unit is in the second position such that a member of a tubular fitting, which tubular fitting is inserted into the holder assembly, protrudes at least partially out of the housing (e.g. through a through hole of the housing) when the tubular fitting is connected to a connector that is inserted into the body of the unit and such that said member is arranged inside the housing (e.g. in a compartment surrounded by the housing) when said tubular fitting is disconnected from said connector, wherein said member is configured to be actuated so as to open or close the tubular fitting (or catheter) for allowing or preventing the passage of fluid through the tubular fitting. Particularly, when the holder assembly is non-moving, the tubular fitting may also be configured to slide with respect to the holder assembly, so that said member can be retracted into the housing or pushed out of the housing.

Further, particularly, the apparatus may be configured to prevent retracting of the tubular fitting for disconnecting the latter from the connector (e.g. by preventing retracting of the holder assembly into the housing) when the tubular fitting clamp (e.g. said member of the tubular fitting described herein) is not closed.

Hence, to ensure safety, the tubular fitting/catheter may be configured such that it cannot be opened for allowing passage of fluid through the fitting/catheter from outside the housing when the tubular fitting is not connected to the connector and is not fastened to an end cap.

Preferably, said member is a rotatable member that is actuated by rotating it (e.g. about an axis along which the tubular fitting or catheter extends), wherein upon rotation of the member the tubular fitting is either closed so that no fluid can pass through the tubular fitting or opened so that fluid can pass through the tubular fitting depending on the direction of said rotation.

Further, particularly, when the cradle assembly or removable unit is in the third position, the cradle assembly is movable towards the holder assembly so as to fasten an end cap received in the opened second receptacle of the capsule to a tubular fitting inserted into the holder assembly so that the tubular fitting is sealed.

Further, particularly, the holder assembly may also be configured to move together with the cradle assembly when the cradle assembly is in the third position such that a member of a tubular fitting, which tubular fitting is inserted into the holder assembly, protrudes—at least partially—out of the housing (e.g. through said through hole of the housing) when the tubular fitting is fastened to an end cap that is received in the opened second receptacle, wherein said member can be actuated so as to close the tubular fitting (or catheter) for preventing passage of fluid through the tubular fitting.

Further, as already described above, the body of the unit/cradle assembly comprises the recess for receiving the first conduit of the connector, which first conduit comprises said frangible inline seal, and for receiving the second conduit (or said single conduit) of the connector, wherein the two conduits branch off from said end section of the connector, via which end section the connector is configured to be connected to a tubular fitting. In case the connector comprises said at least one conduit (e.g. only a single conduit), the at least one conduit (e.g. single conduit) is also connected to an end section of the connector. The at least one conduit/single conduit can be curved such that it easily fits into the second region of the recess.

Further, particularly, the apparatus comprises the first actuating member that is configured to be manually actuated to break said frangible inline seal when the cradle assembly or removable unit is in the second position and a connector inserted into the connector holder is connected to a tubular fitting inserted into the holder assembly. Preferably, the first actuating member comprises a pushable button arranged on the housing (particularly on the cover), wherein upon pushing said button, the first actuating member moves downwards and breaks said frangible inline seal of the first conduit arranged in the first region of the recess.

Further, particularly, the apparatus comprises said second actuating member that is configured to be manually actuated to interrupt the passage of fluid through the first conduit of the connector arranged in the second region of the recess when the cradle assembly or removable unit is in the second position and the connector inserted into the recess of the connector holder is connected to a tubular fitting inserted into the holder assembly. Preferably, the second actuating member comprises a pushable button arranged on the housing (particularly on the cover), wherein upon pushing said button, the second actuating member moves downwards and pushes the first conduit into said slot so that the first conduit is interrupted.

Further, particularly, the apparatus comprises a third actuating member that is configured to be manually actuated to interrupt the passage of fluid through the second conduit of the connector being arranged in the second region of the recess when the cradle assembly or removable unit is in the second position and the connector inserted into the recess of the connector holder is connected to a tubular fitting inserted into the holder assembly.

Further, the third actuating member preferably comprises a pushable button arranged on the housing (particularly on the cover), wherein upon pushing said button, the third actuating member moves downwards and pushes the second conduit into the associated slot so that the second conduit is interrupted.

Preferably, the first conduit is connected to a fluid bag and the second conduit to a fluid waste bag.

Further, particularly, due to said latching noses, the buttons and/or actuating members are configured to remain in a different (e.g. lower position) after they have been pushed by a user, e.g. in order to indicate to the patient/user that they have already been operated.

Particularly, all the three buttons stay in a half-down or down position when pushed during the therapy in order to indicate to the patient that they have already been operated.

Further, particularly, the apparatus comprises a guiding means for guiding said movement of the cradle assembly towards and away from the holder assembly as described above. Further, particularly, said guiding means may also be configured for guiding said movement of the holder assembly.

Further, particularly, the apparatus comprises an actuating means for actuating said means for operating the cradle assembly (and particularly the holder assembly when the holder assembly can move). Preferably, said actuating means comprises a handle for manually actuating said means from outside the housing.

Further, particularly, said means for operating the cradle assembly and particularly holder assembly can comprise a drive or motor that is configured to automatically move the cradle assembly between said positions, and wherein particularly said drive or motor is configured to automatically move the cradle assembly in each of said positions towards and away from the holder assembly in a direction perpendicular to said transverse direction.

Further, particularly, the apparatus can comprise an electronic control unit for controlling said drive or motor, wherein said electronic control unit is preferably programmable in an embodiment so that said automatic movement of the cradle assembly (and particularly holder assembly) is programmable.

Further, particularly, the apparatus may comprise an antibacterial radiation source (e.g. an ultraviolet light source) for reducing contamination with germs.

Further, particularly, the apparatus may comprise a surface comprising a disinfectant admixture, particularly comprised by a coating of said surface or an additive to a molding material of said surface in order to reduce contamination with germs.

Yet a further aspect of the present invention relates to a removable capsule that is particularly configured to be used with a unit or apparatus according to the present invention. The capsule can also be used with an apparatus according to the present invention that comprises a unit that cannot be removed from the apparatus.

According thereto, a capsule for use with a unit, particularly a unit according to the present invention, is disclosed, wherein the capsule comprises a receptacle and an end cap (e.g. of a tubular fitting, particularly of a tubular fitting according to the present invention) arranged in said receptacle, wherein the capsule is configured to be connected to a body of the unit in a releasable fashion.

Particularly, the capsule can comprise the features already described above.

Particularly, in an embodiment of the capsule according to the present invention, the capsule comprises a lateral wall surrounding said receptacle of the capsule (also denoted as second receptacle herein).

Particularly, in an embodiment of the capsule according to the present invention, the lateral wall of the capsule comprises at least one latching nose that is configured to engage with an associated latching recess formed in said lateral wall of said recess for receiving the capsule, or wherein the lateral wall of said recess for receiving the capsule comprises at least one latching nose that is configured to engage with an associated latching recess formed in said lateral wall of the capsule.

Particularly, in an embodiment of the capsule according to the present invention, the capsule comprises an indicator that is configured to indicate whether the capsule is unused.

Particularly, in an embodiment of the capsule according to the present invention, said end cap is completely arranged in said receptacle. Particularly, the capsule encloses the end cap (e.g. hermetically).

Particularly, in an embodiment of the capsule according to the present invention, said receptacle of the capsule is closed, particularly hermetically closed, by a closure comprising a peel-off seal, which peel-off seal is particularly attached to a circumferential face side of the lateral wall of the capsule.

Particularly, in an embodiment of the capsule according to the present invention, said closure comprises a flexible strip connected to the peel-off seal, which strip comprises a free end section that forms a handle by means of which the peel-off seal can be peeled off the lateral wall of the capsule, particularly from outside or inside a housing of an apparatus to which the unit is connectable or connected (see also above), wherein particularly said free end section is configured to be arranged between a bottom and a cover of said housing such that the free end section of the strip protrudes out of the housing.

Particularly, in an embodiment of the capsule according to the present invention, a flexible carrier member, particularly a sponge, that carries an anti-bacterial agent or fluid, is in contact with said end cap and is arranged in the second receptacle of the capsule.

Particularly, in an embodiment of the capsule according to the present invention, said end cap comprises a disinfectant, wherein particularly said end cap is at least partially or completely formed out of said disinfectant, or comprises a coating comprising said disinfectant.

Furthermore, the end cap that is enclosed by the capsule according to the present invention can comprise the features of the end cap according to the present invention describe herein.

The foregoing and other aspects and features of the disclosure will become apparent to those of reasonable skill in the art from the following detailed description, as considered in conjunction with the accompanying drawings.

Figure 2:
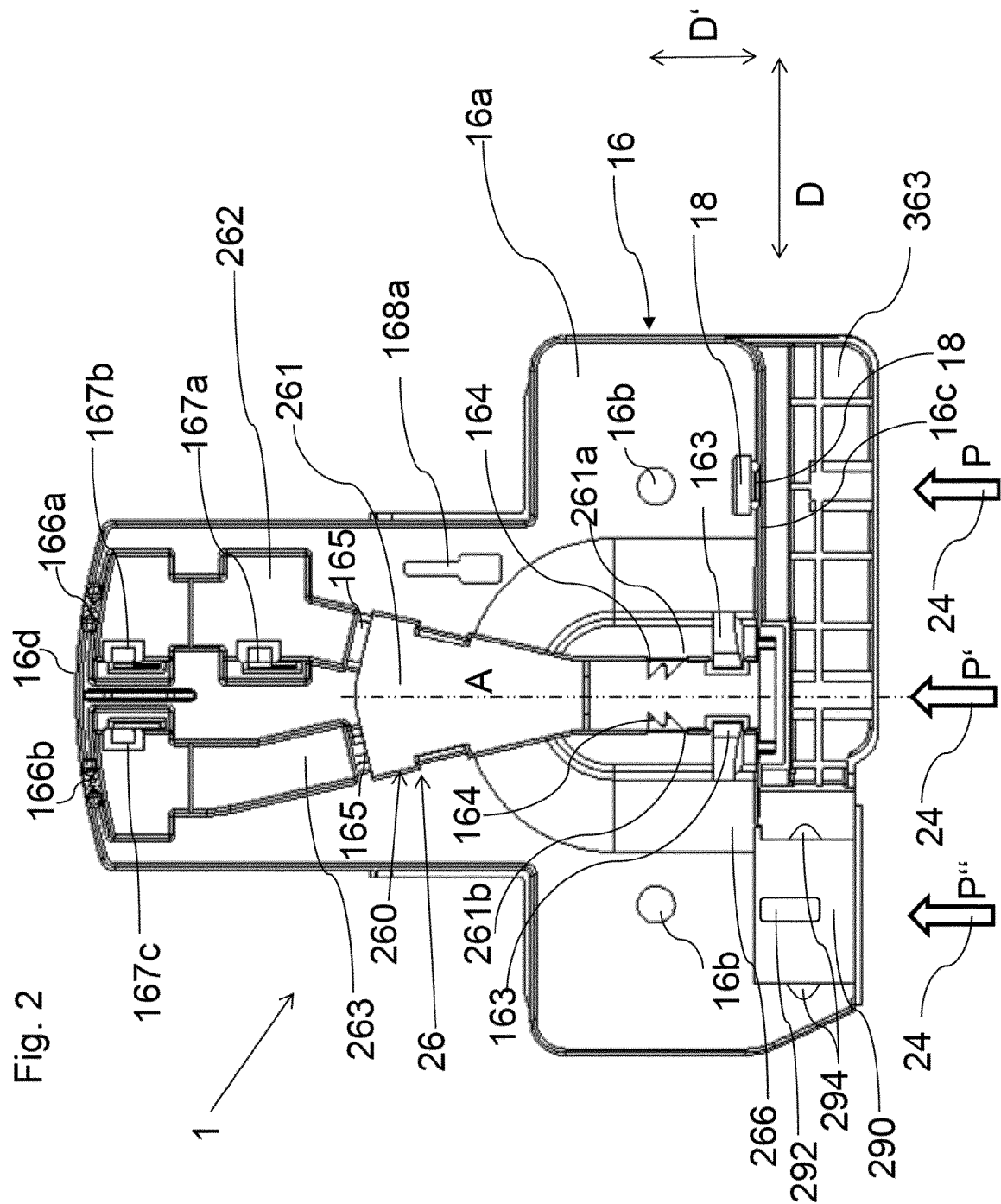
Figure 3:
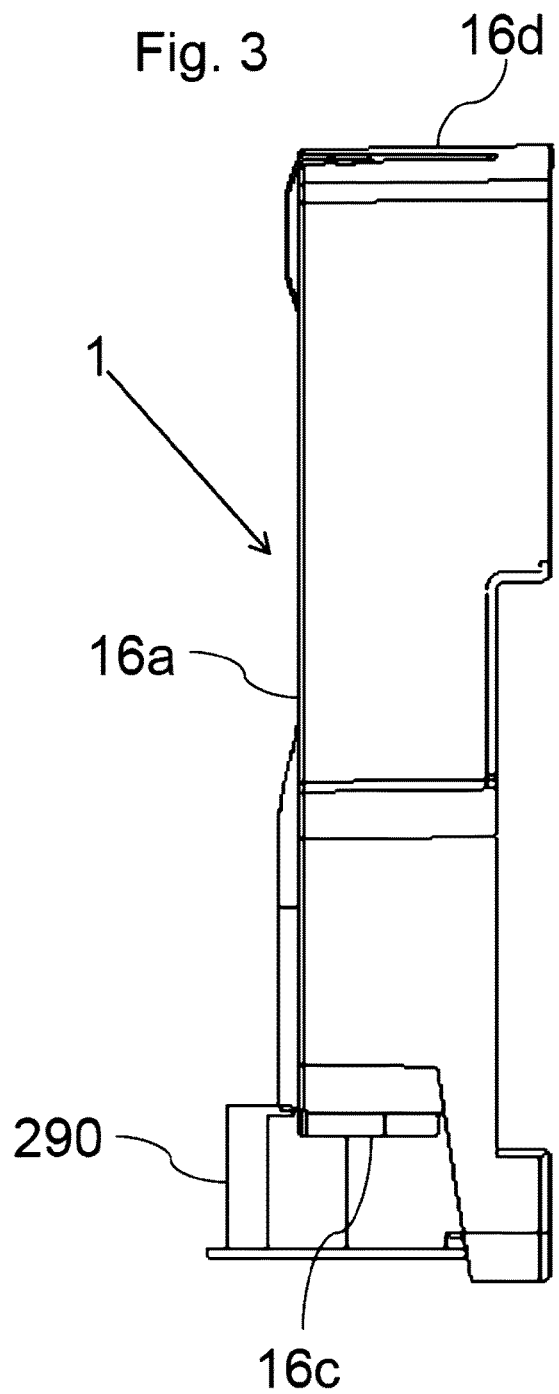
Figure 4:
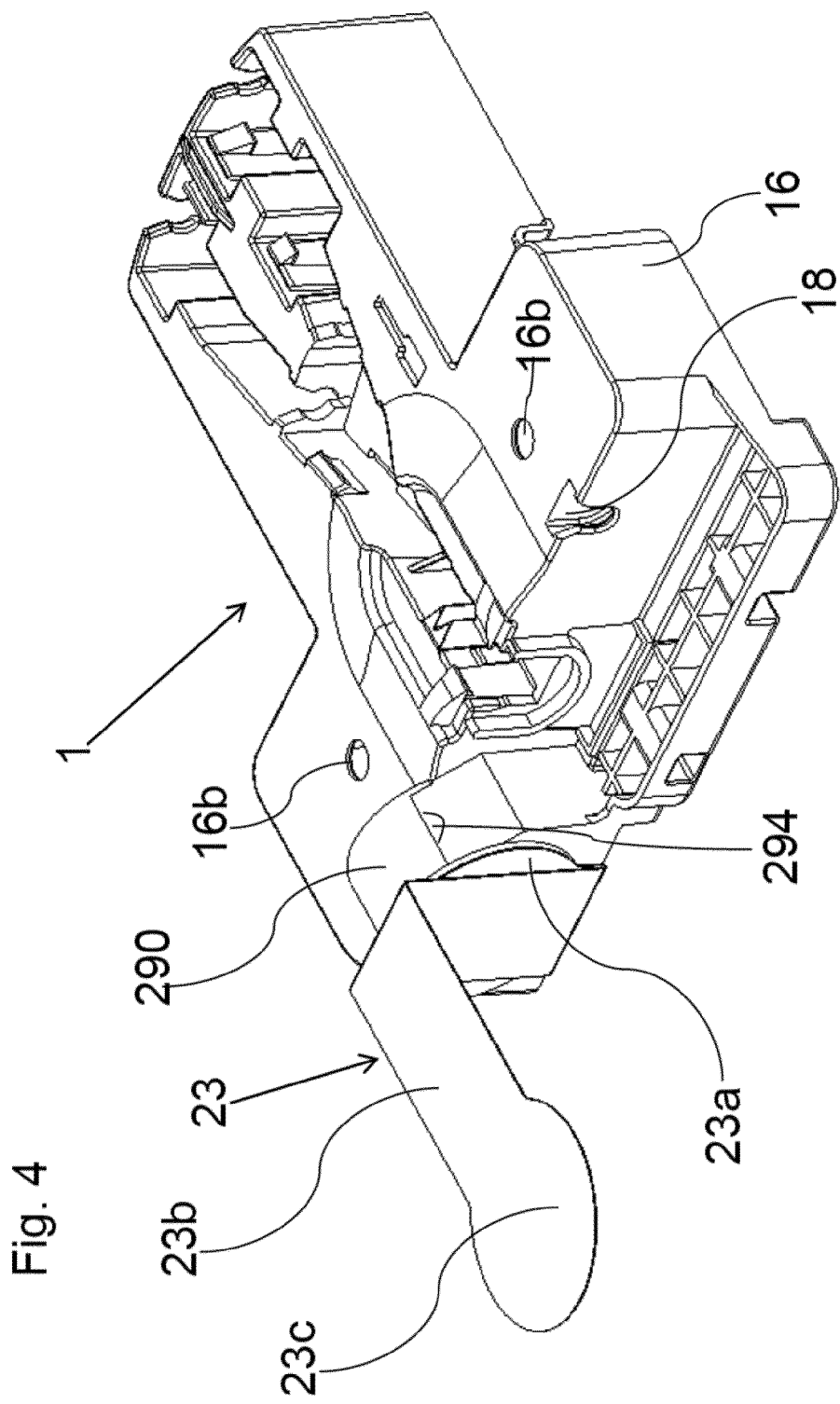
Figure 8:
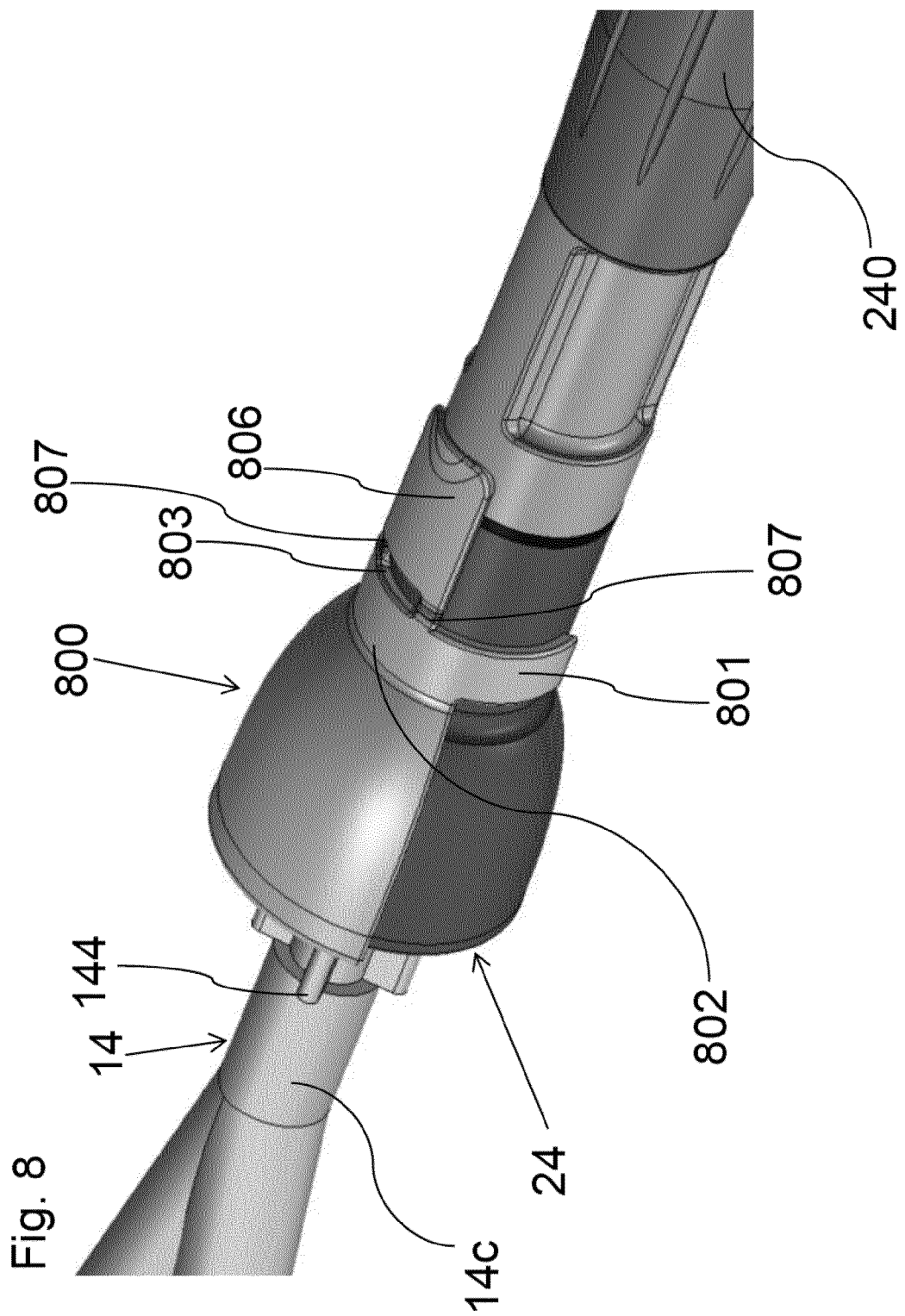
Figure 9:
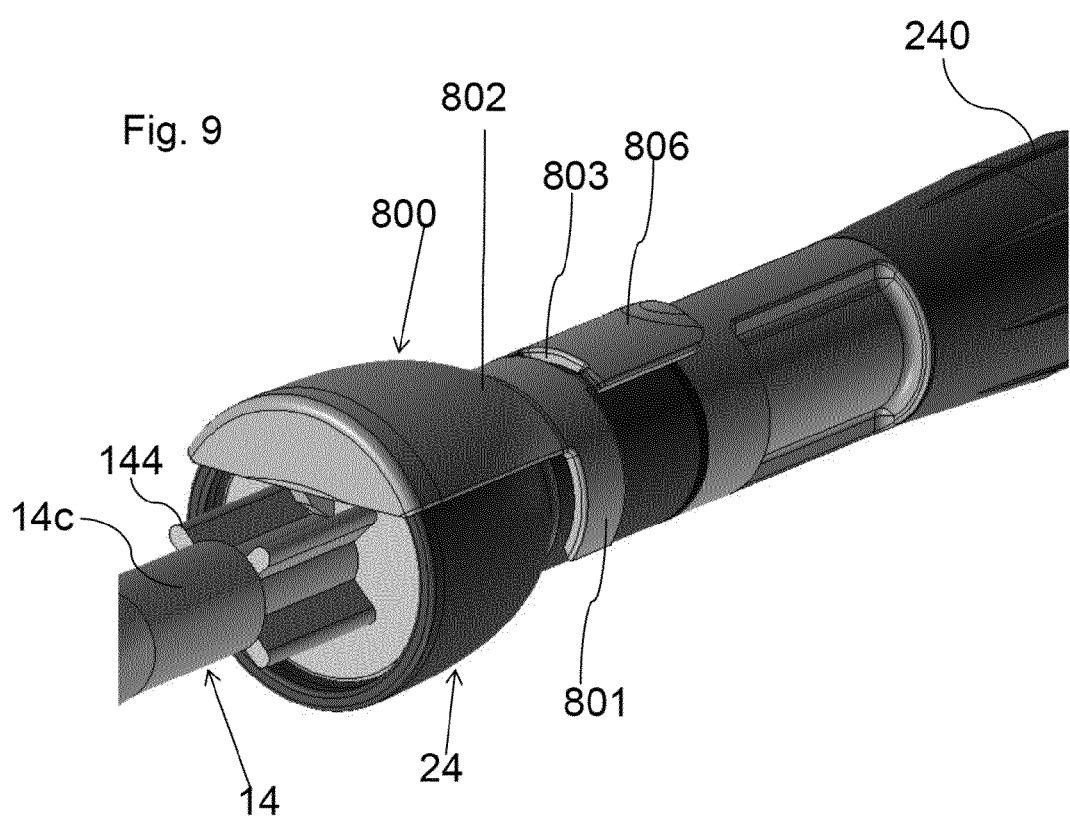
Figure 10:
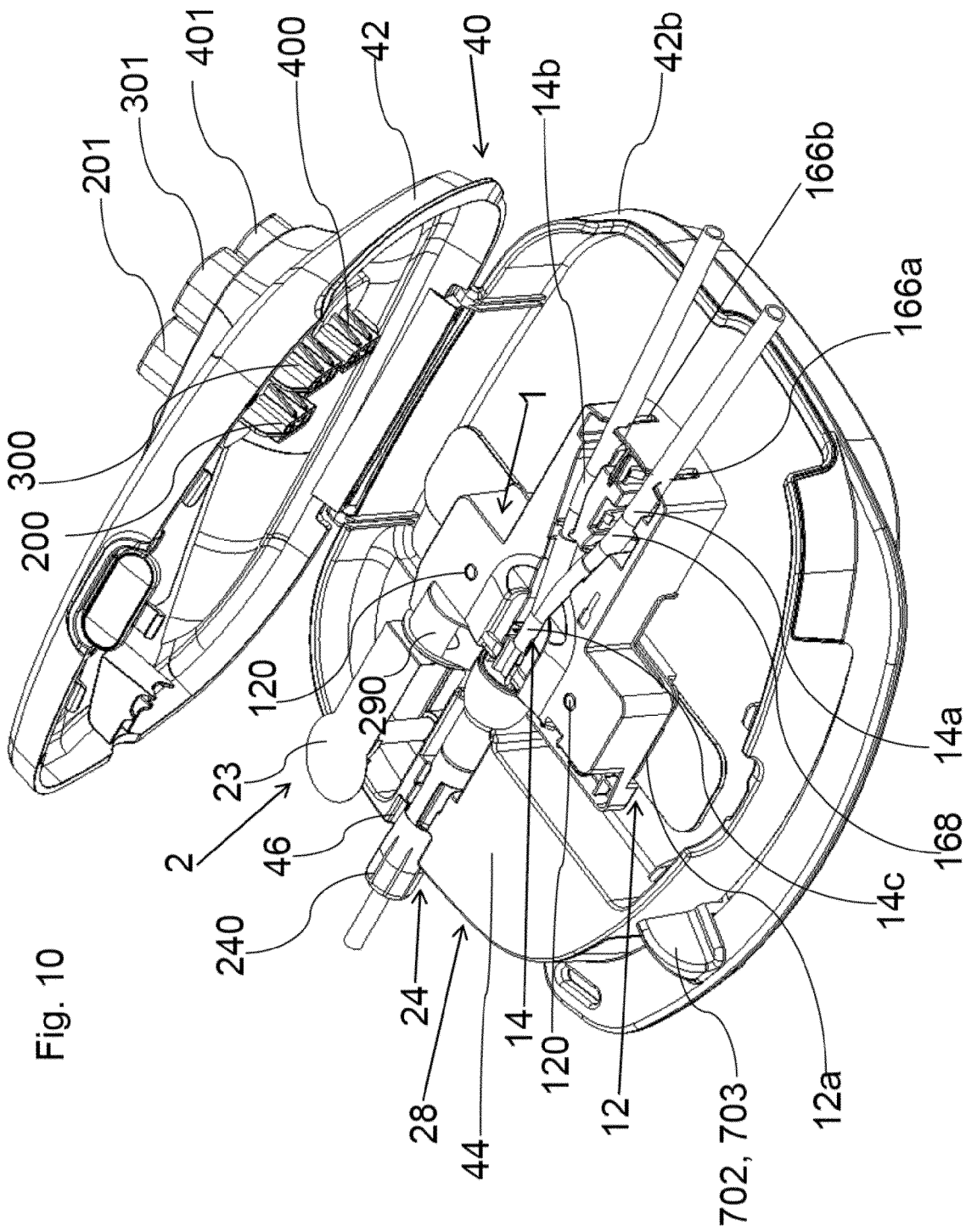
Figure 11A:
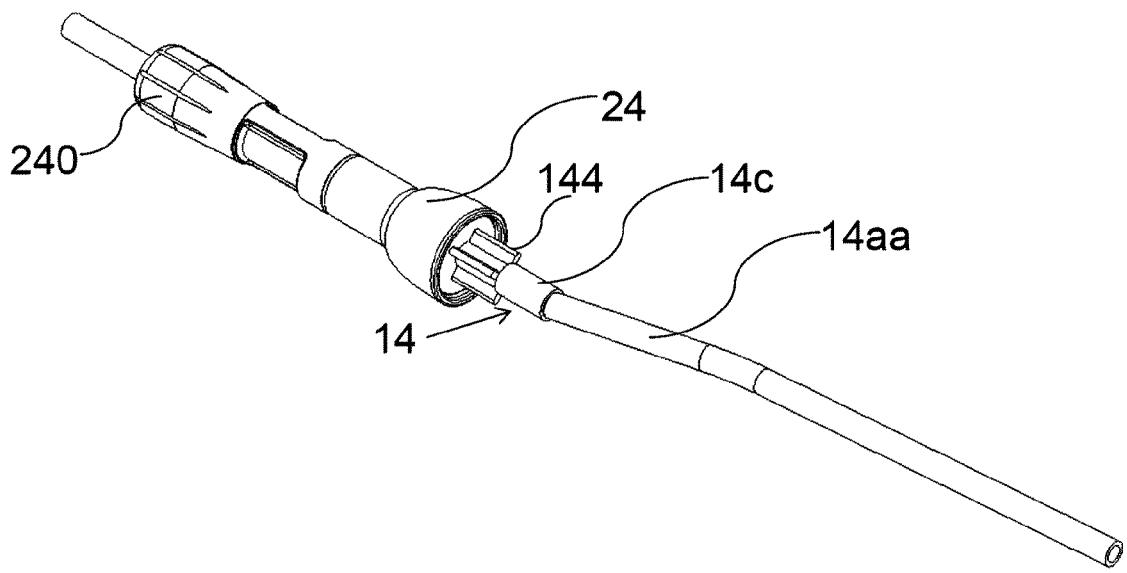
Figure 11B:
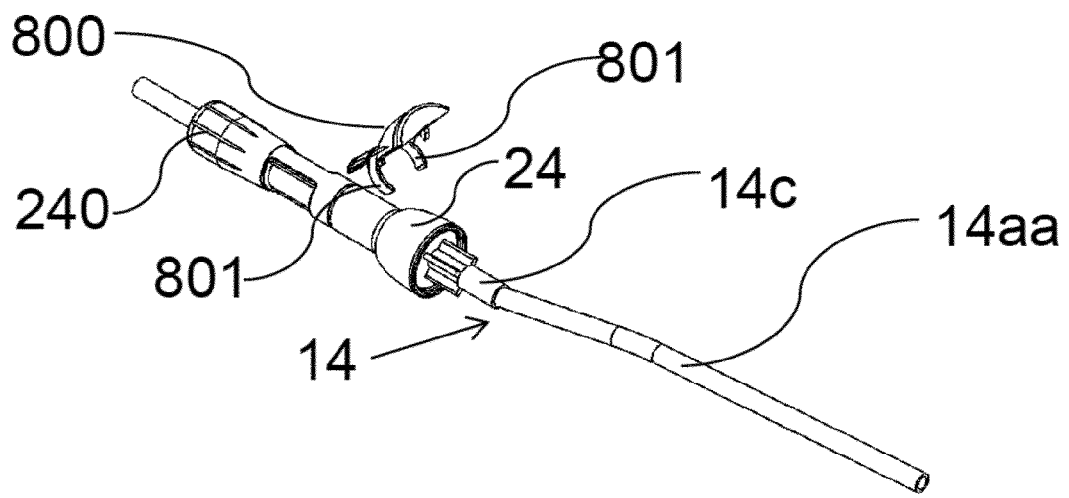
Figure 11C:
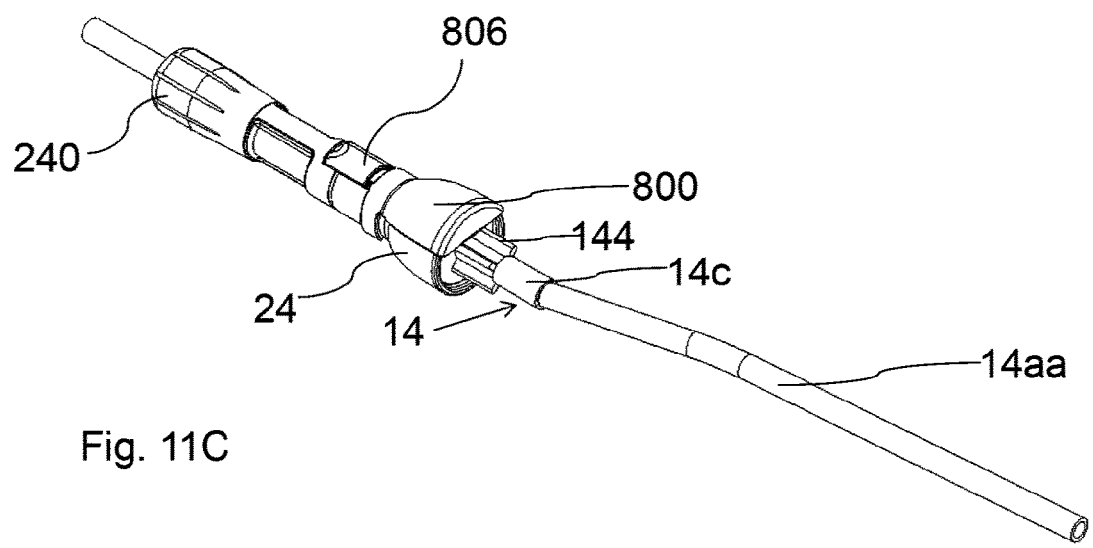
Figure 12:
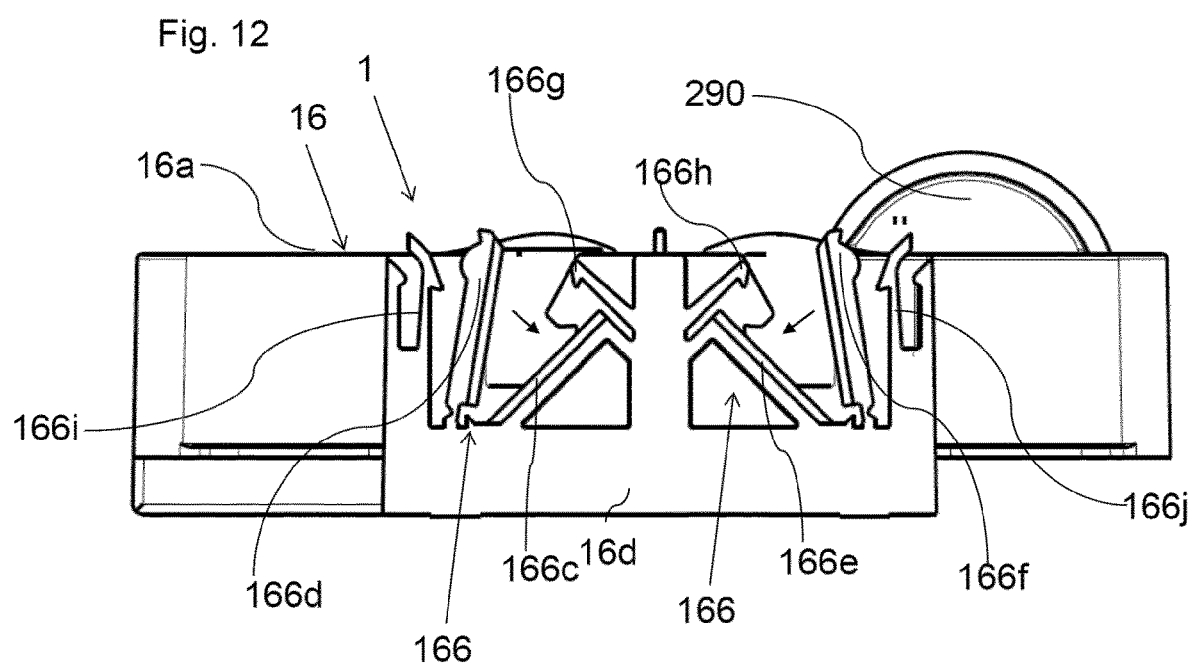
Figure 13:
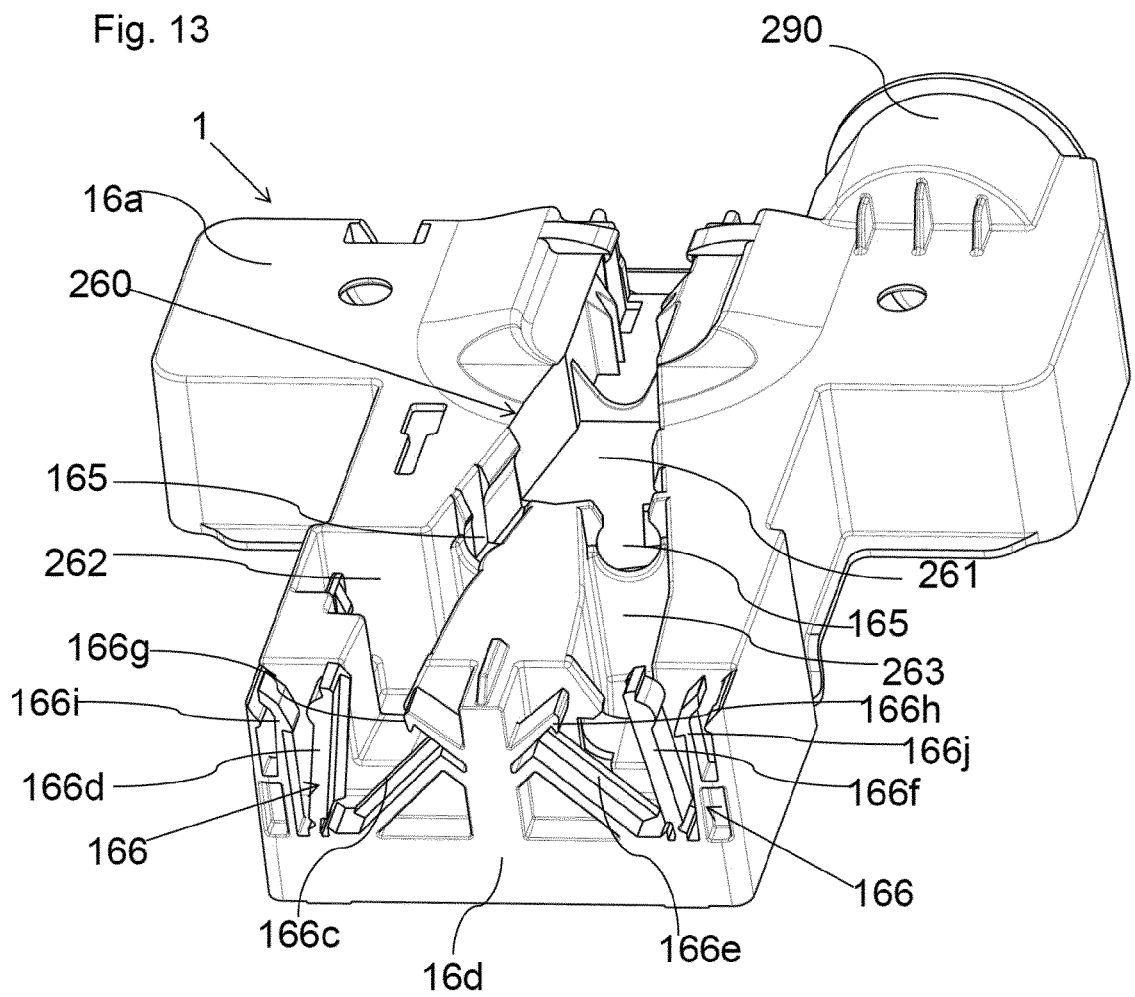

FIG. 1 shows a perspective view of an (e.g. removable) unit according to the invention having a disposable capsule for holding an end cap, FIG. 2 shows a plan view onto a unit according to the invention, FIG. 3 shows a lateral view onto a unit according to the invention, FIG. 4 shows a perspective view onto the unit of FIG. 1 wherein the second receptacle is closed with a peel-off seal, FIG. 5A to 5F show an end cap that can be stored in the second receptacle of the (disposable) capsule, FIG. 6 shows an exploded view of the removable unit of FIG. 4, FIGS. 7 to 9 show a tubular fitting according to the invention comprising a removable clamp, FIG. 10 shows a perspective view of an apparatus for connecting/disconnecting a tubular fitting and a connector that is equipped with a removable unit according to the present invention, FIG. 11A to 11C show a further connector which comprises only a single conduit (e.g. for APD), FIG. 12 shows a view of the back side wall of a removable unit according to the present invention with holding means comprising pivotable clamping arms; and FIG. 13 shows a perspective view of the unit shown in FIG. 12.

FIG. 1 shows together with FIGS. 2 to 6 an e.g. removable unit 1 for an apparatus 2 for connecting and disconnecting a tubular fitting 24 to a connector 14. An example of such an apparatus 2 in shown in FIG. 10, where the unit 1 is connected to a moveable carrier 12a of the apparatus 2.

According to FIGS. 1 to 3, the unit 1, which can be configured to be discarded after e.g. a single or a finite number of uses comprises a body 16 having: a first receptacle 18 and a second receptacle 20, wherein each of said receptacles is configured for receiving/holding an end cap 22 of the tubular fitting 24; and a connector holder 26 being e.g. disposed between said first and second receptacles 18, 20 or between said first receptacle 18 and the recess 20b/capsule 290 (see below), and configured for accommodating insertion of the connector 14.

An embodiment of such an end cap 22 is shown in FIGS. 5A to 5F. Particularly, the end cap 22 comprises a protrusion 22a having a broadened head 22b (cf. FIGS. 5E and 5F) that is configured to engage behind an edge 18a of the first receptacle 18, so that the tubular fitting 24 can be pulled off an end cap 22 when the latter has its head 18b engaged with said edge 18a of the first receptacle 18. Further, particularly, in an embodiment, the end cap 22 comprises an inner protrusion 22c for receiving the protrusion 610 of the tubular fitting 24 (cf. FIGS. 7 to 9 and description below).

Figure 7:
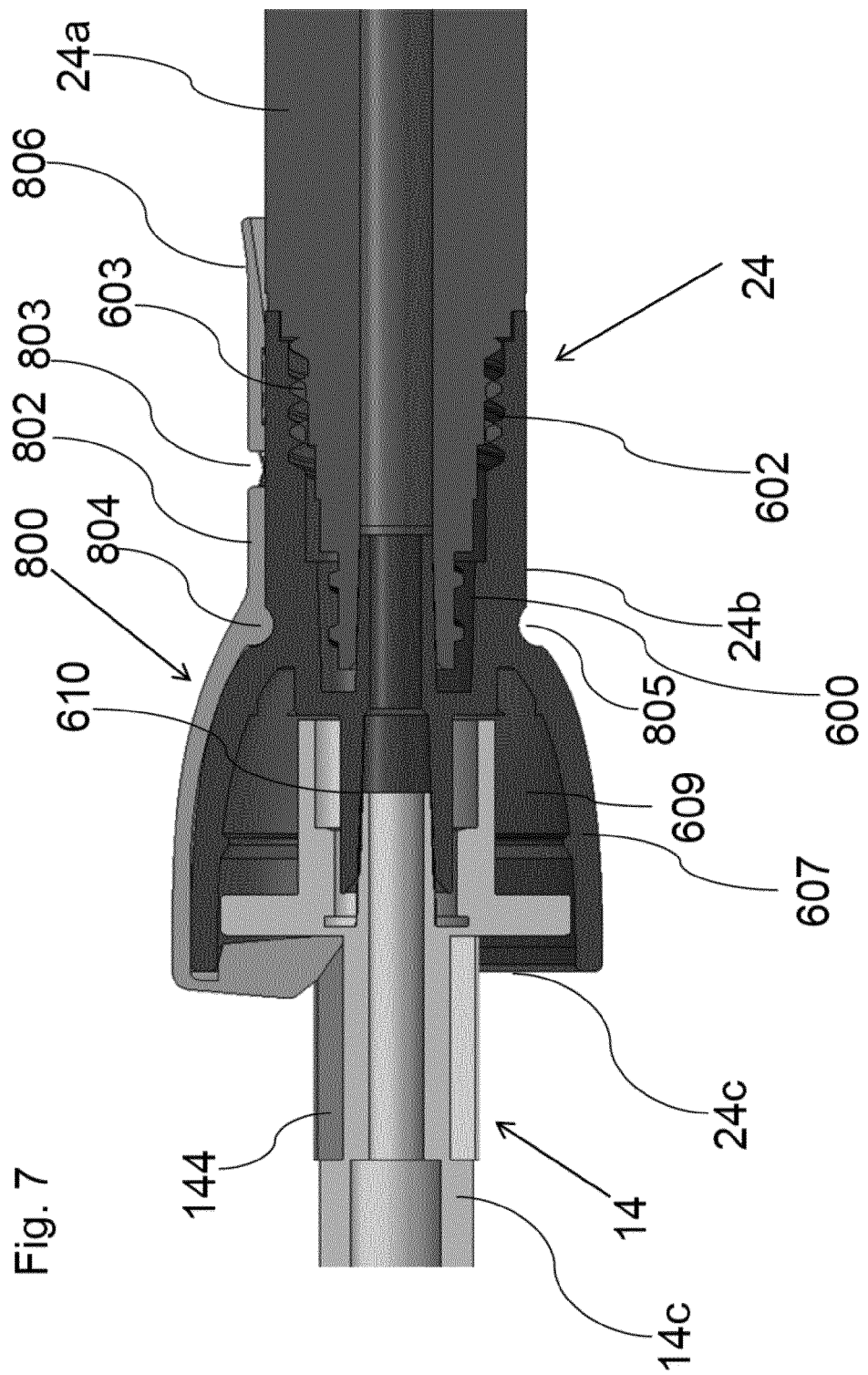

Further, FIGS. 7 to 9 show a typical tubular fitting 24 that is used with the unit 1/apparatus 2.

Particularly, in order to remove the unit 1 from the carrier 12a and a surrounding housing 40 comprising a bottom 42b to which the carrier 12a is mounted and an (e.g. transparent) cover 42 in an easy manner, said body 16 of the removable unit 1 (which may also be denoted as a consumable in the framework of the present invention) is configured to be connected to said apparatus 2 in a releasable fashion, e.g. by means of a latching connection that can be manually established or released.

As already indicated above, the unit 1 is particularly designed for a finite number of uses, each use comprising unfastening an end cap 22 from the tubular fitting 24, connecting the connector 14 inserted into the connector holder 26 of the removable unit 1 to the tubular fitting 24, disconnecting the connector 14 from the tubular fitting 24, and fastening an end cap 22 received in the second receptacle 20 of the capsule 290 to the tubular fitting 24. These basic steps will be described in more detail below (see also above).

As indicated in FIGS. 1 and 6, the unit 1 comprises an end cap 22 for closing the tubular fitting 14 after use, which end cap 22 replaces an old end cap 22 that has been unfastened from the tubular fitting 24 before. According to FIGS. 1 and 6, the fresh and particularly sterile end cap 22 for replacement is arranged in the second receptacle 20 that is formed by a disposable capsule 290 that can be releasably fastened to the body 16 of the unit 1, wherein said end cap 22 is completely arranged in said second receptacle 20.

Particularly, the body 16 comprises a recess 20b for receiving the capsule 290 in a form fitting manner, wherein the capsule 290 and/or the body 16 are configured to fasten the capsule 290 to the body 16 by a latching connection when the capsule 290 is arranged in said recess 20b. Particularly, the recess 20b for receiving the capsule 290 comprises a lateral wall 20c for enclosing the capsule 290 at least partially when the capsule 290 is arranged in said recess 20b. As indicated in FIG. 1, the lateral wall 20c comprises a discontinuity 20d arranged between two opposing edges 20e of the lateral wall 20c on the top side 16a of the body 16 of the unit 1.

In an embodiment, a recess 294 may formed in each edge 20e, which recesses 294 face each other. These recesses 294 allow for a more easy removal of the capsule 290 from the recess 20b since they particularly increase flexibility of the edges 20e that retain the inserted capsule 290.

Alternatively, an actuating member 294 may be arranged at each edge 20e for unlocking the latching connection between the capsule 290 and the recess 20b/lateral wall 20c when the capsule 290 is received in said recess 20b.

Furthermore, the capsule 290 comprises a lateral wall 291 surrounding said second receptacle 20 as well as a bottom connected (e.g. integrally) to the lateral wall 291 of the capsule 290. Particularly, the lateral wall 291 of the capsule 290 comprises at least one latching nose 292 that is configured to engage with an associated latching recess 293 formed in said lateral wall 20c of said recess 20b for receiving the capsule 290. Alternatively, the lateral wall 20c of said recess 20b for receiving the capsule 290 comprises at least one latching nose 293 that is configured to engage with an associated latching recess 292 formed in said lateral wall 291 of the capsule 290. Said latching noses/recesses may form part of the latching connection/mechanism for fastening the capsule 290 in its recess 20b.

Furthermore, as indicated in FIG. 1 for example, the capsule 290 may comprise an indicator 292 that is configured to indicate whether the capsule 290 is unused (e.g. comprises a fresh end cap 22, see also above). Particularly, said indicator 292 is arranged on the lateral wall 291 of the capsule 290 and can be a window or an indicator 292 that undergoes a visually perceivable change when the capsule 290 has been used.

Furthermore, in order to protect the end cap 22 in said second receptacle 20, said second receptacle 20 is closed, particularly hermetically closed, by a closure 23 that is shown in FIGS. 1, 4, 6, and 10. Particularly, the closure 23 comprises a peel-off seal (e.g. foil) 23a, which peel-off seal 23a is attached to a circumferential face side 20a of the capsule 290/lateral wall 291 of the capsule 290 (cf. FIG. 1). Further, said closure 23 comprises a flexible strip 23b connected to the peel-off seal 23a, which strip 23b comprises a free end section 23c which may be configured to be arranged between the bottom 42b and the cover 42 of the housing 40 of said apparatus 2 such that the free end section 23c of the strip 23b protrudes out of the housing 40 and thus forms a handle (having e.g. a flat circular shape) by means of which the peel-off seal 23a can be peeled off the capsule 290 from outside said housing 40 by simply pulling on the free end section 23c (e.g. with two fingers).

For further protection of the end cap 22, the unit 1 can comprise a flexible carrier member 25, particularly a sponge 25, that carries an anti-bacterial agent or fluid, and is in contact with said end cap 22 and also arranged in the second receptacle 20 (together with the end cap 22). Particularly, the flexible carrier member 25 can be inserted into the end cap 22 as shown in FIG. 5A, particularly into said inner cylindrical protrusion 22c of the end cap 22.

As already indicated above, the body 16 of the unit 1 is configured to be connected to said movable carrier 12a of said apparatus 2 (cf. FIG. 10) in a releasable fashion, wherein particularly said carrier 12a is movable with respect to the bottom 42b of the housing 40 of the apparatus 2 so that the removable unit 1 can be moved together with said carrier 12a inside said housing 40 in the different positions P, P', and P'' that will be described in more detail below with reference to FIGS. 2 and 10.

Further, the body 16 comprises a top side 16a, wherein two (e.g. circular) through-holes 16b are formed in the body 16 on the top side 16a which are each configured to receive an associated pin 120 that protrudes from said carrier 12a (cf. FIG. 10) when the body 16 is connected to the carrier 12a, wherein particularly a face side of the respective pin 120 is flush with the top side 16a when the removable unit 1 is connected properly to the carrier 12a of the apparatus 2.

Furthermore, in order to have the connector 14 inserted correctly, the top side 16a comprises a through-hole 168a (e.g. having a contour in the form of a frangible inline seal) which indicates the position of a frangible inline seal 168 of a first conduit 14a of the connector 14.

Particularly, for establishing said releasable connection between the body 16 and the carrier 12a, the body 16 comprises two opposing internal surfaces 160 (cf. schematic detail of FIG. 1 in dashed circle) wherein said internal surfaces face each other, and wherein a latching means 161, particularly a latching nose, is provided on each internal surface for engaging with a complementary latching means, particularly a recess 161a, of the carrier 12a.

Further, the body 16 comprises a front side wall 16c which faces a tubular fitting 24 that shall be connected to the connector 24 or disconnected from the connector 14 and an opposing back side wall 16d (cf. e.g. FIG. 1) via which the conduits 14a, 14b of the connector 14 exit the apparatus 2.

Furthermore, the connector holder 26 comprises a recess 260 (cf. e.g. FIG. 2) for receiving the connector 14 as shown in FIG. 10, which recess 260 is arranged on the top side 16a of the body 16 and extends from the front side wall 16c to the back side wall 16d of the body 16.

Particularly, said recess 260 for receiving the connector 14 comprises an end region 261 extending from the front side wall 16c in the direction of the back side wall 16d, which end region 261 then branches out into a first and a second region 262, 263 of the recess 260 that extend from said end region 261 to the back side wall 16d, respectively.

As can be seen in FIG. 1, at least a portion of the end region 261 of the recess 260 is surrounded by a slight (rounded) protrusion 266 on the top side 16 a on either side of said portion of the end region 261. This protrusion 266 helps the user to place/insert the connector 14 correctly into the recess 260.

Particularly, the Y-shape of the recess 260 allows insertion of a Y-shaped connector 14 (cf. FIG. 10) into the single regions 261, 262, 263 of the recess 260, which connector 14 comprises a first conduit 14a and a second conduit 14b, wherein the two conduits 14a, 14b branch off from an end section 14c of the connector 14, via which end section 14c the connector 14 is configured to be connected to said tubular fitting 24, wherein the end region 261 is configured to receive said end section 14c of the connector 14, and wherein the first region 262 is configured to receive the first conduit 14a, and wherein the second region 263 is configured to receive the second conduit 14b.

Alternatively, as shown in FIGS. 11A to 11O, (e.g. in case of APD), the connector comprises only a single conduit 14aa connected to the end section 14c of the connector 14, which single conduit 14aa is configured to be arranged in the second region 263.

For properly holding the connector 14 in the recess 260, the connector holder/recess 260 comprises a plurality of holding means, which will be described in more detail in the following.

Particularly, as shown in FIGS. 1 and 2, the removable unit 1 comprises an e.g. U-shaped protrusion 162 protruding from the front side wall 16c and extending along the end region 261 of the recess 260 on the front side wall 16c, wherein said protrusion 162 is configured to an inclination of the end section 14c of the connector 14 with respect to an axial direction A of the end section 14c when said end section 14c is inserted in said end region 261 of the recess 260, particularly said protrusion 162 comprises two opposing parallel sections 162a that are integrally connected by a lower curved section 162b which parallel sections 162a and curved section 162b are configured to butt against said end section 14c in a form fitting manner to prevent said inclination.

Further, according to an embodiment, the end region 261 of the recess 260 may comprise an (e.g. rectangular) cross sectional contour 260c in a plane perpendicular to said axial direction A, wherein the end section 14c of the connector 14 comprises a shape in the region of said contour 260c so that the connector 14 cannot be rotated about the axial direction A when it is inserted into the recess 260. Particularly said shape of the connector 14 may be formed by four wings 144 that protrude from the end section 14c and engage with said contour 260c of the recess 260.

Further, the body 16 comprises two holding means or parts 163 arranged on the top side 16a of the body 16, wherein the two holding means 163 are arranged on opposing side walls 261a, 261b of the end region 261 of the recess 260 for holding the end section 14c of the connector 14 in place in the end region 261 of the recess 260 when said end section 14c is arranged in said end region 261 of the recess 260.

Particularly, each of said two holding means 163 comprises a free end, wherein the respective free end protrudes past the associated side wall 261a, 261b of the end region 261 of the recess 260, which two side walls 261a, 261b of said end region 261 of the recess 260 face each other. Thus, the fee ends of the holding means 162 can engage over an end section 14c of the connector 14 that is inserted into the end region 261 of the recess 260 to hold the end section 14c in place in the recess 260.

Furthermore, particularly, the body 16 comprises two holding means or parts 164, wherein each of said holding means 164 forms a tooth structure 164, and wherein the respective tooth structure protrudes from an associated sidewall 261a, 261b of the end region 261 of the recess 260, wherein said two sidewalls 261a, 261b, and tooth structures 164 face each other. Thus, the tooth structures 164 can clamp the end section 14c of the connector from both sides and are thus configured to prevent a movement of the end section 14c of the connector 14 in an axial direction A when said end section 14c of the connector 14 is arranged in said end region 261 of the recess 260 and a force pulls said end section 14 in said axial direction A and into the teeth of the tooth structures 164. Other abrasive structures may also be used.

Furthermore, the body 16 comprises a holding means or part 165 arranged in the first region 262 of the recess 262, which holding means 165 is configured to clamp the first conduit 14a of the connector 14 when said first conduit 14a is arranged in the first region 262 of the recess 260 to hold the first conduit 14a in place, particularly without hindering fluid flow through the first conduit 14a. Particularly said holding means 165 comprises a curved edge for tightly encompassing the first conduit 14a.

In the same manner, the body 16 particularly comprises another holding means or part 165 arranged in the second region 263 of the recess 260, which holding means 165 is in turn configured to clamp the second conduit 14b of the connector 14 (or said single conduit 14aa, cf. FIGS. 11A to 11C) when said second conduit 14b is arranged in the second region 263 of the recess 260 to hold the second conduit 14a in place, particularly without hindering fluid flow through the first conduit 14a. Particularly, also here, said holding means 165 comprises a curved edge for tightly encompassing the second conduit 14b.

Furthermore, particularly, the body 16 comprises a holding means or part 166 arranged in the first region 262 of the recess 260 at the back side wall 16d, which holding means 166 is configured to clamp the first conduit 14a of the connector 14 when said first conduit 14a is arranged in the first region 262 of the recess 260, wherein particularly said holding means 166 is configured to encompass said first conduit, e.g. by means of a curved edge for tightly encompassing the first conduit 14a. Further, said holding means 166 comprises a slot 166a extending from said edge into which slot 166a the first conduit 14a can be pushed so that the first conduit 14a is blocked for the passage of fluid through the first conduit 14a.

Likewise, the body 16 further comprises such a holding means or part 166 arranged in the second region 263 of the recess 260 at the back side wall 16d, which holding means 166 is in turn configured to clamp the second conduit 14b of the connector 14 when said second conduit 14b is arranged in the second region 263 of the recess 260, particularly by means of a curved edge for tightly encompassing the second conduit 14b. Also here said holding means 166 of the second region 263 comprises a slot 166b extending from said edge, into which slot the second conduit 14b can be pushed so that the second conduit 14b is blocked for the passage of fluid through the second conduit 14b.

The actuating members 200, 300, 400 (cf. FIG. 10) by means of which the frangible seal 168 can be broken and the conduits 14a, 14b can be blocked will be described in detail below.

FIGS. 12 and 13 show alternative holding means 166 which may be used instead of the holding means 166 comprising said slots 166a and 166b.

Particularly, here, the holding means 166 of the first region 262 of the recess 260 comprises a clamping surface 166c and a pivotable clamping arm 166d, wherein the clamping arm 166d can be pivoted towards the particularly inclined clamping surface 166c into a clamping position so that the first conduit 14a (cf. FIG. 10) is blocked when it is clamped between said clamping surface 166c and the clamping arm 166d.

Analogously, the holding means 166 arranged in the second region 263 of the recess 260 at the back side wall 16d, can comprises a clamping surface 166e and a pivotable clamping arm 166f, too, wherein the clamping arm 166f is in turn configured to be pivoted towards the clamping surface 166e into a clamping position so that the second conduit 14b or said at least one conduit 14aa is blocked when it is clamped between said clamping surface 166e and said clamping arm 166f.

Further, the clamping arm 166d of the holding means 166 of the first region 262 of the recess 260 can be configured to be pivoted towards the associated clamping surface 166c by means of the second actuating member 300 of the apparatus 2 (see also below and FIG. 10). Likewise, the clamping arm 166f of the holding means 166 of the second region 263 of the recess 260 can be configured to be pivoted towards the associated clamping surface 166e by means of the third actuating member 400 of the apparatus 2 (see also below and FIG. 10).

Furthermore, the respective holding means 166 may comprise a hook 166g, 166h for engaging with the respective clamping arm 166d, 166f so as to hold the respective clamping arm 166d, 166f in its clamping position. When the respective arm 166d, 166f is engaged with the respective hook 166g, 166g, the respective conduit 14a, 14b, 14aa is clamped between the associated clamping surface 166c, 166e and the associated clamping arm 166d, 166f and is therefore blocked.

Furthermore, each holding means 166 may comprise a guiding arm 166i, 166j for guiding a movement of the respective second or third actuating member 300, 400 upon pivoting the respective clamping arm 166d, 166f towards the associated clamping surface 166c, 166e.

Particularly, in FIG. 13, the capsule 290 may also form an integral part of the body 16 of the unit 1 that cannot be removed from the body 16 (see also above).

Furthermore, the body 16 comprises a first and a second latching nose 167a, 167b at the first region 262 of the recess 260, wherein the respective latching nose 167a, 167b is configured to engage an associated (first and second) actuating member 200, 300 of the apparatus 2 so as to hold the respective actuating member 200, 300 in a pressed position. Particularly the first latching nose 167a is configured to engage with a first actuating member 200 of the apparatus 2 that is configured to break said frangible inline seal 168 of the first conduit 14a and to keep the first conduit 14a open for the passage of fluid, and wherein particularly the second latching nose 167b is configured to engage with a second actuating member 300 of the apparatus 2 that is configured to press the first conduit 14a in said slot 166a.

Furthermore, the body 16 comprises a third latching nose 167c at the second region 263 of the recess 260, wherein said third latching nose 167c is configured to engage an associated third actuating member 400 of the apparatus 2 so as to hold said third actuating member 400 in a pressed position. Particularly, the third latching nose 167c is configured to engage with said third actuating member 400 of the apparatus 2 that is configured to press the second conduit 14b in said slot 166b.

Furthermore, in order to protect the apparatus from spilled fluid from the fluid lines that are connected or disconnected by means of the apparatus 2, the removable unit comprises a drip pan 360 that protrudes from the front side wall 16c of said body 16 and is arranged below the end region 261 of the recess 260 as well as below the first receptacle 18 to receive said leakage fluid. Preferably, said drip pan 360 comprises a plurality of dents 363 for receiving said spilled fluid. Which plurality of dents 363 allows to hold and calm the leakage fluid.

Furthermore, the body 16 may comprise a centering means 361 for guiding a movement of the removable unit 1 in the axial direction A, which centering means 361 is arranged (at least in sections) on the drip pan 360. Particularly, said centering means 361 is formed as a recess 361 of the drip pan 360 for receiving a guiding means, particularly a guiding pin 361a of the apparatus 2, which guiding pin 361a is schematically indicated in FIG. 1).

The drip pan 360 preferably comprises a recess 362 that extends parallel to the recess 361 and allows to arrange the removable unit 1 on the carrier 12a in the first position P (this recess 362 then receives the guiding pin 361a).

Furthermore, FIGS. 7 to 9 show an embodiment of a tubular fitting 24 for use with a removable unit 1/apparatus 2 according to the invention, wherein the tubular fitting 24 is configured to be received by an opening 46 of a body 44 of a holder assembly 28 of said apparatus 2 as indicated in FIG. 10.

As shown in FIGS. 7 to 9, the tubular fitting 24 comprises a first portion 24a and an adjacent second portion 24b comprising an opening 24c. Particularly, the second portion 24b is configured such that an end cap 22 according to the present invention can be fastened to the second portion 24b by plugging the end cap 22 into said opening 24c of said second portion 24b, and wherein the second portion 24b is configured such that an end cap 22 can be unfastened from the second portion 24b by pulling the end cap 22 out of said opening 24c. Please note that an end cap 22 is not shown in FIGS. 7 to 9, but can replace the connector 14 shown in FIGS. 7 to 9 when the connector is removed from the tubular fitting 24.

Further, particularly, the second portion 24b is configured such that the connector 14 can be connected to the second portion 24b by plugging the connector 14 into said opening 24c of said second portion 24b, and wherein the second portion 24b is configured such that a connector 14 can be disconnected from the second portion 24b by pulling the connector 14 out of said opening 24c.

Furthermore, the tubular fitting 24 comprises a removable clamp 800 (cf. e.g. FIGS. 7 and 8) for arresting the connector 14 with respect to the second portion 24b when the connector 14 is connected to the second portion 24b, wherein particularly the clamp 800 is configured to be connected to the second portion 14b, particularly by means of a clip-on connection, wherein particularly the clamp 800 encompasses the second portion 24b when it is connected to the second portion 24b.

For this, the clamp 800 preferably comprises curved arms 801 (cf. also FIGS. 11A to 11O) extending from a base 802 of the clamp 800 in a peripheral direction of the second portion 24b for tightly encompassing the second portion 24b which establishes the clip-on connection.

Furthermore, the clipped-on clamp 800 covers a portion of the shroud 607/opening 24c and of said opening 24c when the clamp 800 is connected to the second portion 24b, wherein the clamp 800 is configured to engage behind a portion of the connector 14 when the connector 14 is connected to the second portion 24b so that the connector 14 cannot be disconnected from the second portion 24b.

Furthermore, for defining a location of the clamp 800 on the second portion 24b, the clamp 800 comprises a protrusion 804 for insertion into a circumferential groove 805 of the second portion 24b when the clamp 800 is connected to the second portion 24b.

Further, the clamp 800, comprises a through-hole 803 in a region where the arms 801 project from the base 802, such that a flap 806 is formed that is hinged to the base 802 in a flexible manner (e.g. via integral hinges 807 on either side of the hole 803). This allows to remove the clamp 800 manually from the tubular fitting 24 by lifting the flap 806 away from the fitting 24.

As shown in FIGS. 7 to 9 the second portion 24b is formed as an adapter (or the tubular fitting 24 is formed as an adapter when the first portion 24a is not considered as a component of the tubular fitting/adapter 24, but as a part of a catheter etc.), which comprises a first recess 600 at a first end of the adapter 24b, which first recess 600 comprises an internal thread 602 configured to be rotationally fastened to an external thread 603 of the first portion 24a, and wherein the adapter 24b comprises a shroud 607 at an opposite second end of the adapter 24b, which shroud 607 surrounds a second recess 609 of the adapter 24b into which a protrusion 610 of the adapter 24b protrudes, which protrusion 610 comprises said opening 24c of the adapter 24b such that the shroud 607 surrounds said protrusion 610 and said opening 24c of the adapter 24b, wherein the shroud 607 is coaxially arranged with respect to said protrusion 610.

Alternatively, the first and second portion 24a, 24b may be integrally connected to one another.

FIG. 10 shows the unit 1 when installed into the apparatus 2. As shown in FIG. 10 the apparatus 2 comprises a means for operating said cradle assembly 12, which means may comprise an actuating means 702 that may comprise a handle 703 that is accessible from outside said housing 40 of the apparatus 2 so that said cradle assembly 12, particularly the removable unit 1 is reciprocable (or can be moved back and forth) in a (transverse) first direction D (cf. FIGS. 1 and 2) relative to said holder assembly 28 between a first position P, a second position P', and a third position P'''. These positions with respect to the tubular fitting 24 that is inserted into the holder assembly 28 are indicated in FIG. 2 with arrows.

The cradle assembly 12 may be guided by a guiding means and said means for operating the cradle assembly 12 may be configured to e.g. mechanically transform a force on an actuating element 702 comprising particularly a handle 703 for manual actuation by a user into a linear movement of the cradle assembly 12 (and particularly holder assembly 28) between the positions P, P', and P'''. Means 30 may also comprise a drive such as an (e.g. electrical) motor 31, particularly for moving the cradle assembly 12 between said positions P, P', P'''. The actuating element 702, 703 may then be configured for triggering said drive.

Further, said holder assembly 28 includes a body 44 having an opening 46 for receiving the tubular fitting 24. The tubular fitting 24 may comprise recesses for engaging with the body 44 in the region of said opening 46 of the body 44. Further, particularly when the holder assembly 28 is non-moving, the tubular fitting 24 can be allowed to slide back and forth in the opening 46 in the axial direction A. However, in the embodiment shown in FIG. 10, the tubular fitting 24 cannot move in the axial direction A with respect to the holder assembly 28.

Furthermore, as indicated in FIG. 2, the cradle assembly 12/unit 1 is configured to be movable in each of said positions P, P', P''' towards and away from the holder assembly 28 by means of said means for operating the cradle assembly (e.g. by using said actuating means 702 and particularly handle 703) in a second direction D' running perpendicular to said first direction D. Other ways of actuation are also conceivable.

Particularly, when the cradle assembly 12/unit 1 is in the first position P, as indicated in FIG. 2, the cradle assembly 12 is movable away from the holder assembly 28 (cf. FIG. 10), so as to unfasten an end cap 22 received in the first port 18 that is fastened to the tubular fitting 24 from said tubular fitting 24, which in turn is inserted into the holder assembly 28, namely in the corresponding opening 46 (cf. FIG. 10).

From there, the cradle assembly 12/unit 1 is moveable into the second (transverse) position P' as well as towards the holder assembly 28 so as to connect a connector 14 inserted into the connector holder 26/recess 260 to the tubular fitting 24 so that a flow connection can be established between the tubular fitting 24 and the connector 14. When the fluid delivery procedure (which will be described below) is over, the cradle assembly 12/removable unit 1 is moveable away from the holder assembly 28 as indicated by the arrow D' shown in FIG. 2, so as to disconnect the connector 14 from the tubular fitting 24.

As further shown in FIG. 10, the apparatus 2 comprises an openable or removable cover 42 of the housing 40. The cover 42 is preferably at least partially or completely transparent, particularly so as to be able to observe the fastening/unfastening of the end caps 22 and the connecting of the tubular fitting 24 to the connector 14 as well as the disconnecting of the tubular fitting 24 from the connector 14.

Further, the holder assembly 28 may be configured to let the tubular fitting 24 move or slide with the cradle assembly 12/removable unit 1 when the cradle assembly 12 is in the second position, such that a member 240 of the tubular fitting 24 protrudes at least partially out of the housing 40 (this member 240 is also shown in FIGS. 27 and 28), e.g. through a through hole 41 formed in the housing 40. Thus, the member 240 is accessible from outside the housing 40 when the tubular fitting 24 is connected to the connector 14 so that the tubular fitting 24 can be opened (e.g. by rotating member 240) and fluid can pass the tubular fitting 24. However, here, particularly, the tubular fitting 24 is non-moving in the axial direction A and said member 240 protrudes out of the housing 40 regardless of the position/movement of the removable unit 1.

Further, as indicated in FIG. 2, when the cradle assembly 12/unit 1 is in the second position P' and is moved away from the holder assembly 28, the tubular fitting 24 may also move with the cradle assembly 12 in the beginning so that said member 240 is again positioned inside a compartment defined by the housing 40 and cannot be rotated from outside the housing 40 to ensure that the tubular fitting 24 that has been closed by means of member 240 before disconnecting the tubular fitting 24 from the connector 14 cannot be opened again so that fluid can be lost.

Further, from the second position shown in FIG. 2, the cradle assembly 12 is movable into the third position P''' and towards the holder assembly 28 so that a new end cap 22 that is arranged in the second receptacle 20 can be fastened to the tubular fitting 24. In this position, the member 240 protrudes again or still out of the housing 40 through opening 41.

Before the new end cap 22 can be fastened to the tubular fitting 24, the peel-off seal 23a described above is removed from the capsule 290 that has been inserted into the recess 20b in beforehand, so that the end cap 22 is accessible for a connection with the tubular fitting 24 (see also above).

Furthermore, for operating the connector 14, the apparatus 2 comprises said recess 260 formed on the top side 16a of the body 16 of the removable unit 12.

When the tubular fitting 24 has been connected to the connector 14 as intended (e.g. FIG. 10), the first actuating member 200 is pressed via a button 201 so that said frangible inline seal 168 is broken.

This allows flushing of the conduits 14a, 14b while the tubular member 24 is still closed. Thus fluid (e.g. from a fluid bag) enters the first conduit 14a, is passed into the second conduit 14b and ends up e.g. in a fluid waste bag connected to the second conduit 14b.

When the conduits 14a, 14b have been flushed, a third actuating member 400 is pressed via a button 401 so as to interrupt the passage of fluid through the second conduit 14b arranged in the second region 262 of the recess 260 of the removable unit 1. To accomplish this, the third actuating member 400 is configured to press the second conduit 14b into the associated slot 166b so that the second conduit 14b is compressed and thereby sealed in the slot 166b. Now, the member 240 is actuated and fluid passes from the first conduit 14a via the tubular fitting 24 to a catheter of the patient.

Finally, to end fluid delivery, the member 240 is actuated to close the tubular fitting 24 and a second actuating member 300 (cf. FIG. 10) is pressed via a button 301 so as to interrupt the passage of fluid through the first conduit 14a being arranged in the first region 262 of the recess 260. Again, to accomplish this, the second actuating member 300 is configured to press the first conduit 14a into the associated slot 166a so that the first conduit 14a is compressed and thereby sealed in the slot 166a.

Now, the connector 14 can be disconnected from the tubular fitting 24 and a new end cap 22 received in the second receptacle 20 can be fastened to the tubular fitting 24 as described above.

Alternatively, as already indicated above, instead of the slots 166a, 166b, the holding means 166 comprising said clamping surfaces 166c, 166e and clamping arms 166d, 166f may be used to block/seal the first, second or at least one conduit 14, 14b, 14aa by actuating the corresponding (second or third) actuating member 300, 400. Here, as already described above, the clamping arm 166d can be pivoted downwards/towards its clamping surface 166c by means of the second actuating member 300 (i.e. by pushing button 301) for sealing the first conduit 14a. Further, the clamping arm 166f can be pivoted downwards/towards its associate clamping surface 166e by means of the third actuating member 400 (i.e. by pushing button 401) for sealing the second conduit 14b or the at least one conduit 14aa.

It is to be noted, that the actuating members 200, 300, 400 are preferably mounted such to the housing 40 or with respect to the recess 260 of the cradle assembly 12/removable unit 1 that the cradle assembly 12 can move relative to the actuating members 200, 300, 400, but the latter are able to engage with the respective conduit 14a, 14b as described above, when the cradle assembly 12 resides in the second position P' and has been moved towards the holder assembly 28 so that the connector 14 is properly connected to the tubular fitting 24.

Preferably, the buttons 201, 301, 401 are labeled by means of a pictogram, respectively, so as to describe their specific function to a user. This allows a description of the function of the buttons 201, 301, 401 that is independent of any language and universally understandable. The buttons may also be labeled by means of numbers that indicate the order of operation of the buttons.

Most preferably, in the framework of the present invention as described herein, the connecting and/or disconnecting of connector 14 and tubular fitting 24 (as well as recapping) is performed by one of: a patient using the apparatus at home (e.g. a home dialysis patient), by a caregiver using the apparatus at the patient's home or within a health care facility, or by a healthcare professional using the apparatus at the patient's home or in a health care facility.

The invention claimed is:

1. A unit (1) for an apparatus (2) for connecting and disconnecting a tubular fitting (24) to a connector (14), comprising:
a body having a first receptacle (18) and a connector holder (26) configured for accommodating insertion of the connector (14), wherein the first receptacle is configured for holding an cap (22), and
a second receptacle (20), of the tubular fitting (24),
wherein
the unit (1) comprises a capsule (290) that is configured to be connected to said body (16) in a releasable fashion, wherein said capsule (290) comprises said second receptacle (20), and wherein the body (16) comprises a recess (20b) for receiving the capsule (290) in a form fitting manner, and wherein the end cap (22) is arranged in said second receptacle (20) formed by the capsule (290), and wherein the capsule (290) comprises a lateral wall (291) surrounding said second receptacle (20), and wherein said second receptacle (20) of the capsule (290) is closed by a closure (23) comprising a peel-off seal (23a), which peel-off seal (23a) is attached to a circumferential face side (20a) of the lateral wall (291) of the capsule (290), and wherein the end cap comprises a protrusion (22a) having a broadened head (22b) that is configured to engage behind an edge (18a) of the first receptacle (18).

2. The unit according to claim 1, characterized in that the capsule (290) and/or the body (16) are configured to fasten the capsule (290) to the body (16) by a latching connection when the capsule (290) is arranged in the recess (20b).

3. The unit according claim 1, characterized in that the recess (20b) for receiving the capsule (290) comprises a lateral wall (20c) for enclosing the capsule (290) at least partially when the capsule (290) is arranged in said recess (20b).

4. The unit according claim 3, characterized in that the lateral wall (20c) comprises a discontinuity (20d) arranged between two opposing edges (20e) of the lateral wall (20c).

5. The unit according claim 4, characterized in that a recess (294) is formed in each edge (20e), which recesses (294) face each other.

6. The unit according to claim 1, characterized in that the unit (1) is a removable unit (1), wherein said body (16) is configured to be connected to said apparatus (2) in a releasable fashion.

7. The unit according to claim 1, characterized in that the unit (1) is configured to be sterilized for allowing multiple uses, or wherein the unit (1) is a disposable unit (1) that is designed for one of: a single use, particularly comprising unfastening an end cap (22) from the tubular fitting (24), connecting the connector (14) inserted into the connector holder (26) to the tubular fitting (24), disconnecting the connector (14) from the tubular fitting (24), and fastening an end cap (22) received in the second receptacle (20) to the tubular fitting (24); a finite number of uses.

8. The unit according to claim 1, characterized in that the end cap (22) is completely arranged in said second receptacle (20).

9. The unit according to claim 1, characterized in that said closure (23) comprises a flexible strip (23b) connected to the peel-off seal (23a), which strip (23b) comprises a free end section (23c) that forms a handle by means of which the peel-off seal (23a) can be peeled off the lateral wall (291) of the capsule (290), particularly from outside or inside a housing (40) of the apparatus (2), wherein particularly said free end section (23c) is configured to be arranged between a bottom (42b) and a cover (42) of said housing (40) such that the free end section (23c) of the strip (23b) protrudes out of the housing (40).

10. The unit according to claim 8, characterized in that a flexible carrier member (25) that carries an anti-bacterial agent or fluid, is in contact with said end cap (22) and is arranged in the second receptacle (20) of the capsule (290).

11. The unit according to claim 8, characterized in that said end cap (22) comprises a disinfectant, wherein particularly said end cap (22) is at least partially or completely formed out of said disinfectant, or comprises a coating comprising said disinfectant.

12. The unit according to claim 1, characterized in that the body (16) is configured to be connected to a movable carrier (12a) of said apparatus (2) in a releasable fashion, wherein particularly said carrier (12a) is movable with respect to the bottom (42b) of the housing (40) of the apparatus (2) so that the unit (1) can be moved together with said carrier (12a) inside said housing (40).

13. The unit according to claim 1, characterized in that the body (16) comprises a front side wall (16c) and an opposing back side wall (16d).

14. The unit according to claim 13, characterized in that the connector holder (26) comprises a recess (260) for receiving the connector (14), which recess (260) is arranged on a top side (16a) of the body (16) and extends from the front side wall (16c) to the back side wall (16d) of the body (16).

15. The unit according to claim 14, characterized in that the recess (260) for receiving the connector (14) comprises an end region (261) extending from the front side wall (16c), which end region (261) branches out into a first and a second region (262, 263) that extend from said end region (261) to the back side wall (16*d*), respectively, wherein said recess (260) for receiving the connector (14) is configured to receive the connector (14), which connector (14) comprises at least one conduit (14*aa*), which is connected to an end section (14*c*) of the connector (14), via which end section (14*c*) the connector (14) is configured to be connected to said tubular fitting (24), wherein the end region (261) is configured to receive said end section (14*c*) of the connector (14), and wherein the second region (263) is configured to receive said at least one conduit (14*aa*), or a first conduit (14*a*) and a second conduit (14*b*), wherein the two conduits (14*a*, 14*b*) branch off from an end section (14*c*) of the connector (14), via which end section (14*c*) the connector (14) is configured to be connected to said tubular fitting (24), wherein the end region (261) is configured to receive said end section (14*c*) of the connector (14), and wherein the first region (262) is configured to receive the first conduit (14*a*), and wherein the second region (263) is configured to receive the second conduit (14*b*).

16. The unit according to claim 13, characterized in that the body (16) comprises a holding means (166) arranged in the first region (262) of the recess (260) at the back side wall (16*d*), which holding means (166) is configured to clamp the first conduit (14*a*) of the connector (14) when said first conduit (14*a*) is arranged in the first region (262) of the recess (260), wherein said holding means (166) comprises a clamping surface (166*c*) and a pivotable clamping arm (166*d*), wherein the clamping arm (166*d*) is configured to be pivoted towards the clamping surface (166*c*) into a clamping position so that the first conduit (14*a*) is blocked when it is clamped between said clamping surface (166*c*) and the clamping arm (166*d*), and/or wherein the body (16) comprises a holding means (166) arranged in the second region (263) of the recess (260) at the back side wall (16*d*), which holding means (166) is configured to clamp the second conduit (14*b*) or said at least one conduit (14*aa*) of the connector (14) when said second conduit (14*b*) or said at least one conduit (14*aa*) is arranged in the second region (263) of the recess (260), wherein said holding means (166) comprises a clamping surface (166*e*) and a pivotable clamping arm (166*0*, wherein the clamping arm (166*0* is configured to be pivoted towards the clamping surface (166*e*) into a clamping position so that the second conduit (14*b*) or said at least one conduit (14*aa*) is blocked when it is clamped between said clamping surface (166*e*) and said clamping arm (166*0*.

17. A capsule (290) for use with a unit (1) according to claim 1, wherein the capsule (290) comprises a receptacle (20) and an end cap (22) arranged in said receptacle (20), wherein the capsule (290) is configured to be connected to a body (16) of the unit (1) in a releasable fashion, and wherein the capsule (290) comprises a lateral wall (291) surrounding said receptacle (20), and wherein said receptacle (20) of the capsule (290) is closed by a closure (23) comprising a peel-off seal (23*a*), which peel-off seal (23*a*) is attached to a circumferential face side (20*a*) of the lateral wall (291) of the capsule (290), and wherein the end cap comprises a protrusion (22*a*) having a broadened head (22*b*) that is configured to engage behind an edge (18*a*) of the first receptacle (18) of the unit (1).

\* \* \* \* \*